(12) United States Patent
Apkarian

(10) Patent No.: US 11,419,857 B2
(45) Date of Patent: Aug. 23, 2022

(54) METHODS AND COMPOSITIONS FOR TREATING PAIN

(71) Applicant: Apkarian Technologies LLC, Chicago, IL (US)

(72) Inventor: A. Vania Apkarian, Chicago, IL (US)

(73) Assignee: Apkarian Technologies LLC, Chicago, IL (US)

( * ) Notice: Subject to any disclaimer, the term of this patent is extended or adjusted under 35 U.S.C. 154(b) by 79 days.

(21) Appl. No.: 16/584,103

(22) Filed: Sep. 26, 2019

(65) Prior Publication Data

US 2020/0046687 A1    Feb. 13, 2020

Related U.S. Application Data

(62) Division of application No. 15/341,700, filed on Nov. 2, 2016, now abandoned.

(60) Provisional application No. 62/249,588, filed on Nov. 2, 2015.

(51) Int. Cl.
| | |
|---|---|
| *A61K 31/428* | (2006.01) |
| *A61K 31/198* | (2006.01) |
| *A61K 31/192* | (2006.01) |
| *A61K 31/167* | (2006.01) |
| *A61K 45/06* | (2006.01) |

(52) U.S. Cl.
CPC .......... *A61K 31/428* (2013.01); *A61K 31/167* (2013.01); *A61K 31/192* (2013.01); *A61K 31/198* (2013.01); *A61K 45/06* (2013.01)

(58) Field of Classification Search
CPC .. A61K 31/167; A61K 31/192; A61K 31/198; A61K 31/428; A61K 45/06
See application file for complete search history.

(56) References Cited

U.S. PATENT DOCUMENTS

| | | | |
|---|---|---|---|
| 5,192,753 A | 3/1993 | McGeer et al. | |
| 5,627,168 A | 5/1997 | Bigge et al. | |
| 6,018,675 A | 1/2000 | Apkarian et al. | |
| 6,228,875 B1 | 5/2001 | Tsai et al. | |
| 6,645,973 B1 | 11/2003 | Gibson et al. | |
| 7,846,913 B2 | 12/2010 | McDevitt et al. | |
| 8,653,120 B2 | 2/2014 | Apkarian | |
| 2002/0111384 A1 | 8/2002 | Boudrie et al. | |
| 2005/0209317 A1 | 9/2005 | Apkarian | |
| 2011/0230513 A1 | 9/2011 | Lamensdorf et al. | |
| 2014/0213621 A1 | 7/2014 | Apkarian | |

FOREIGN PATENT DOCUMENTS

| | | |
|---|---|---|
| WO | WO-98/20864 A2 | 5/1998 |
| WO | WO-01/36423 A1 | 5/2001 |
| WO | WO-03/089411 A1 | 10/2003 |
| WO | WO-2005/092442 A2 | 10/2005 |
| WO | WO 2005/107467 A2 * | 11/2005 |

OTHER PUBLICATIONS

Apkarian, Sep. 26, 2013, "Effect of L-dopa in subacute back pain population" NIH U.S. National Library of Medicine Clinical Trials. (Year: 2013).*
Cohen et al., "Opiate receptor avidity and cerebral blood flow in Alzheimer's disease," J Neurol Sci. 148(2):171-80 (1997).
Henderson et al., "Competitive antagonists and partial agonists at the glycine modulatory site of the mouse N-methyl-D-aspartate receptor," J Physiol. 430:189-212 (1990).
International Preliminary Report on Patentability for International Patent Application No. PCT/IB2005/050983 dated Sep. 26, 2006 (1 page).
International Search Report for International Patent Application No. PCT/IB2005/050983 dated Oct. 12, 2005 (6 pages).
Krystal et al., "NMDA agonists and antagonists as probes of glutamatergic dysfunction and pharmacotherapies in neuropsychiatric disorders," Harv Rev Psychiatry. 7(3):125-43 (1999).
Lauritzen, "Spreading depression and migraine," Pathol Biol (Paris). 40:332-337 (1992) (Abstract Only).
Le Bars et al., "Animal models of nociception," Pharmacol Rev. 53(4):597-652 (2001).
Millan et al., "(+)—HA 966, a partial agonist at the glycine site coupled to NMDA receptors, blocks formalin-induced pain in mice," Eur J Pharmacol. 238(2-3):445-7 (1993).
Millan et al., "Chemically-diverse ligands at the glycine B site coupled to N-methyl-D-aspartate (NMDA) receptors selectively block the late phase of formalin-induced pain in mice," Neurosci Lett. 178(1):139-43 (1994).
Mutschler: "Arzneimittelwirkugen" 2001, WWG, Stuttgart, XPOO2347156.
Parsons et al., "Modulation of NMDA receptors by glycine— introduction to some basic aspects and recent developments," Amino Acids 14(1-3):207-16 (1998).
Pauwels et al., "Ca++ and Na+ channels involved in neuronal cell death. Protection by flunarizine," Life Sci. 48(20):1881-1893 (1991) (Abstract only).
Reckziegel et al., "Gender dependent pharmacotherapy for blocking transition to chronic back pain: a proof of concept randomized trial," medRxiv. 19006627 (2019) (29 pages).
Tan-No et al., "Intrathecally administered D-cycloserine produces nociceptive behavior through the activation of N-methyl-D-aspartate receptor ion-channel complex acting on the glycine recognition site," J Pharmacol Sci. 104(1):39-45 (2007).
Tan-No et al., "Intrathecally administered spermine produces the scratching, biting and licking behaviour in mice," Pain 86(1-2):55-61 (2000).

(Continued)

*Primary Examiner* — Kara R McMillian
(74) *Attorney, Agent, or Firm* — Clark & Elbing LLP

(57) ABSTRACT

The invention features combinations of dopaminergic agents and analgesic agents useful for treating pain. In particular, the combinations feature a low ratio of dopaminergic agent to analgesic agent. The dopaminergic agent can be an agonist of the dopamine receptor D1-like family or the dopamine receptor D2-like family. Such combinations potentiate analgesia to 1) alleviate acute pain, 2) prevent the transition from acute pain to chronic pain, and 3) manage chronic pain.

30 Claims, 19 Drawing Sheets
(17 of 19 Drawing Sheet(s) Filed in Color)

(56) References Cited

OTHER PUBLICATIONS

Tsai et al., "Glycine transporter I inhibitor, N-methylglycine (sarcosine), added to antipsychotics for the treatment of schizophrenia," Biol Psychiatry. 55(5):452-6 (2004).
Woolf, C., "Pain: moving from symptom control toward mechanism-specific pharmacologic management," Ann Intern Med. 140(6):441-51 (2004).
Written Opinion of the International Searching Authority for International Patent Application No. PCT/IB2005/050983 dated Oct. 12, 2015 (12 pages).
Young, "Guidelines promote COX-2 inhibitors for managing chronic pain," Am J Health Syst Pharm. 59(14):1315-6,8 (2002) (4 pages).
Vachon-Presseau et al., "The Emotional Brain as a Predictor and Amplifier of Chronic Pain," J Dent Res. 95(6):605-612 (2016).
Ren et al., "The indirect pathway of the nucleus accumbens shell amplifies neuropathic pain," Nat Neurosci. 19(2):220-222 (2016).

\* cited by examiner

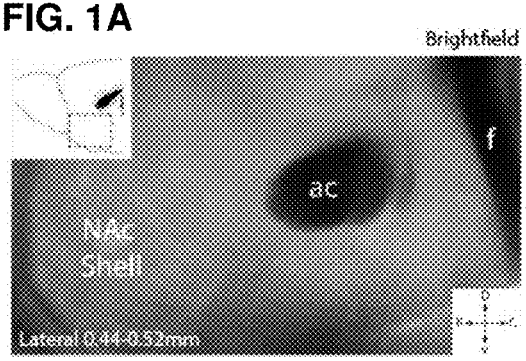
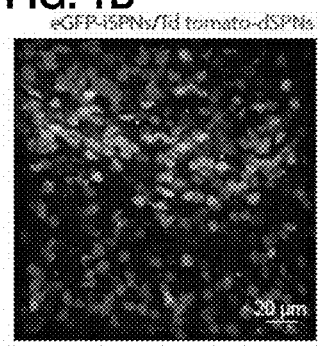
FIG. 1A    FIG. 1B
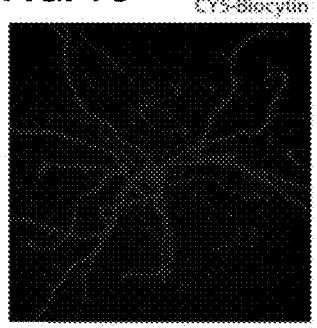
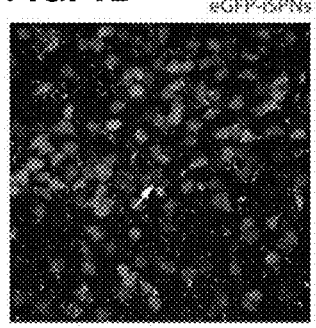
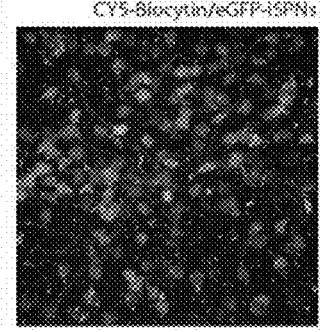
FIG. 1C    FIG. 1D    FIG. 1E
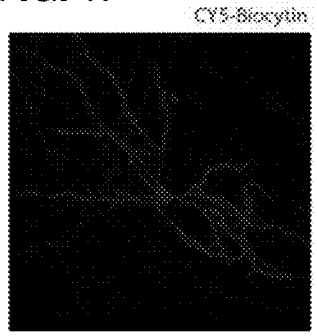
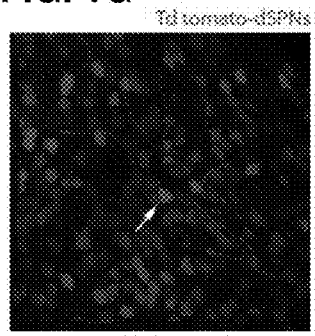
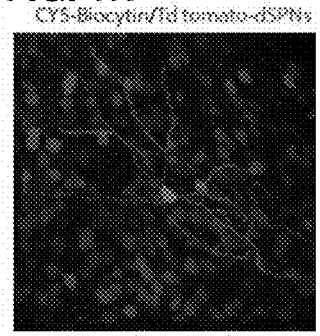
FIG. 1F    FIG. 1G    FIG. 1H

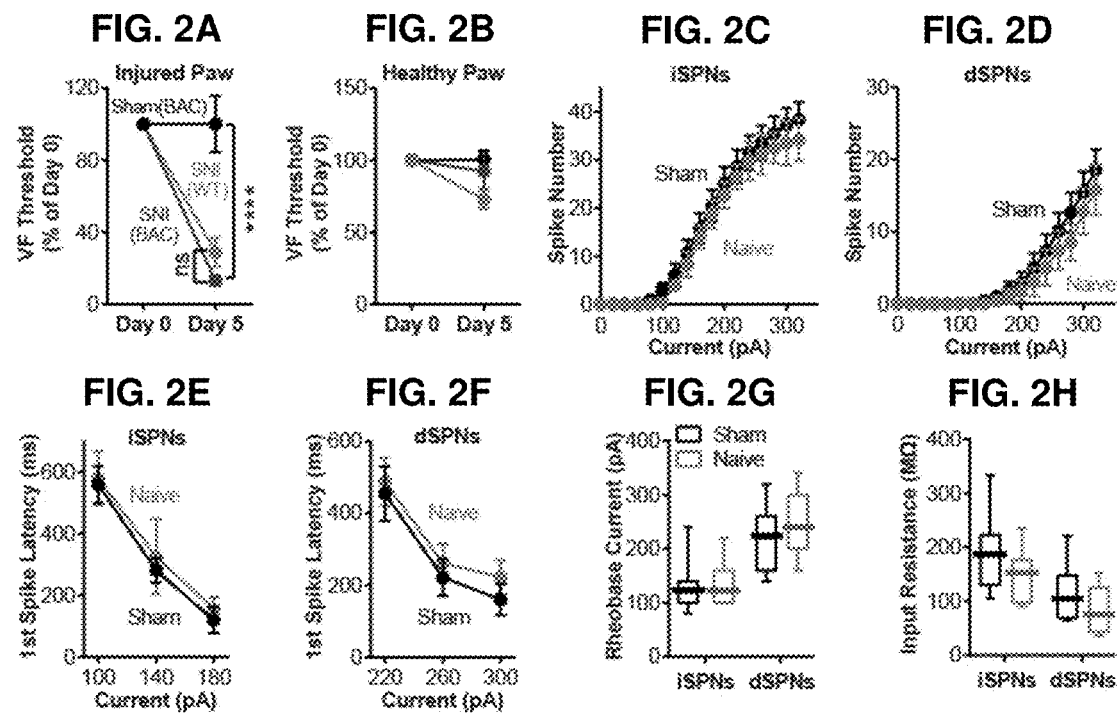

FIG. 3A  FIG. 3B  FIG. 3C
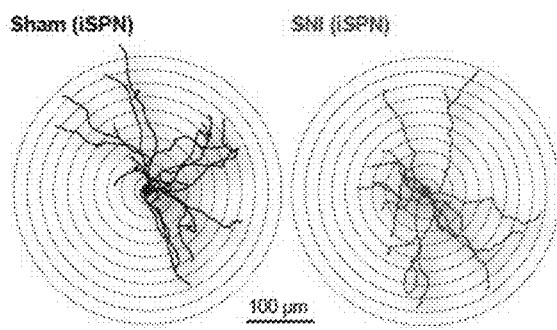
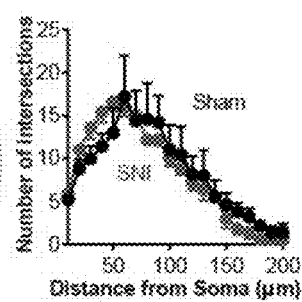
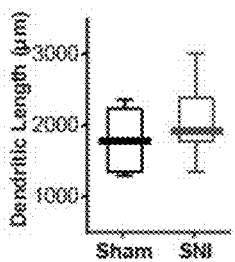
FIG. 3D  FIG. 3E
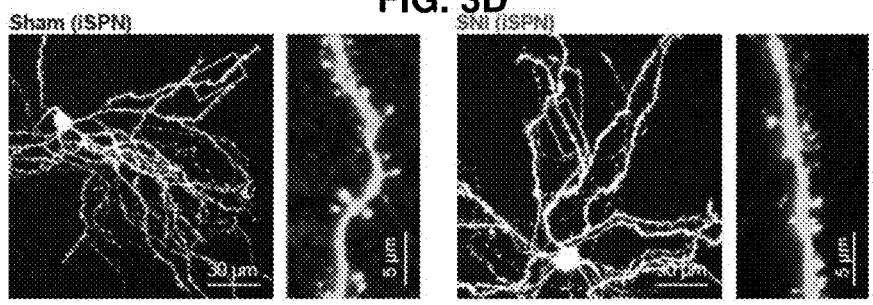
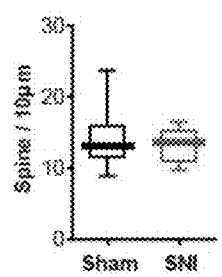
FIG. 3F  FIG. 3G  FIG. 3H
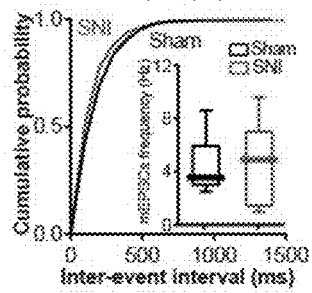
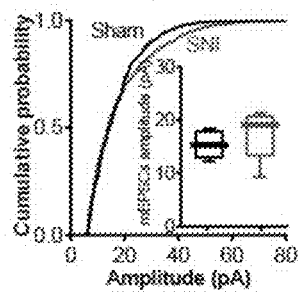

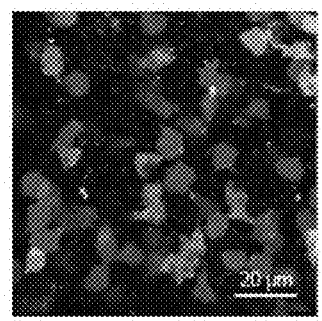
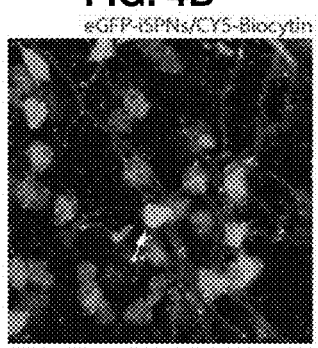
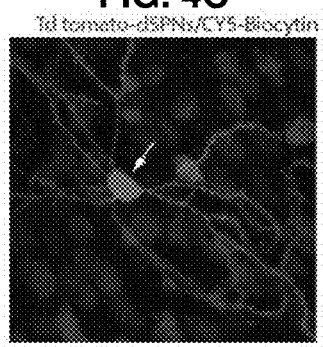
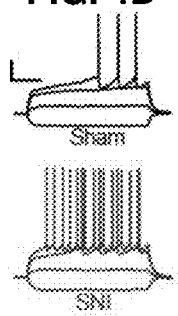
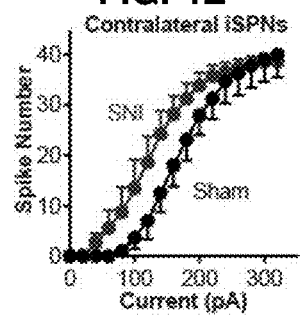
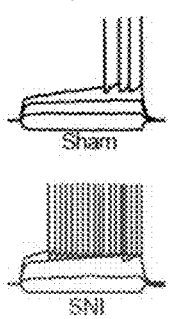
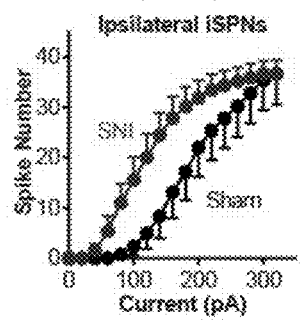
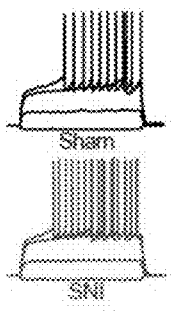
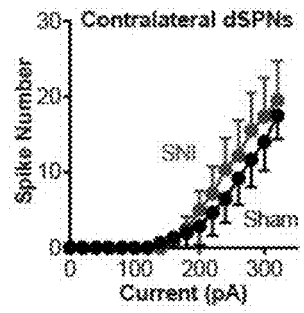
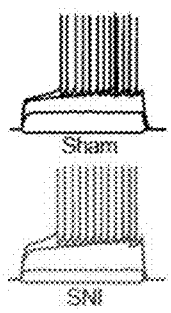
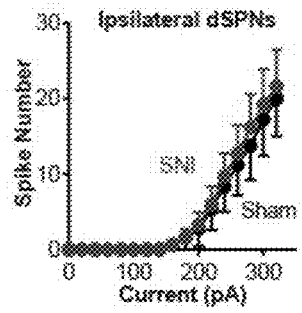
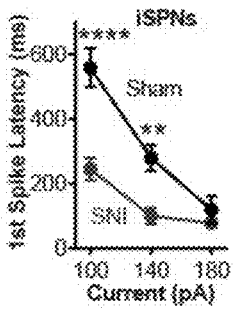
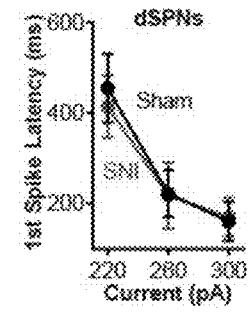
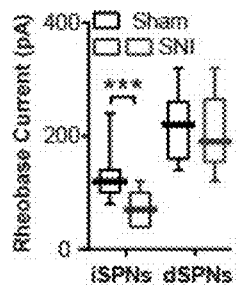
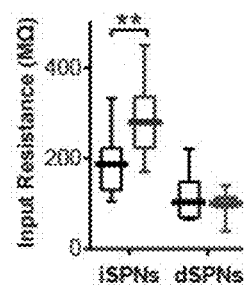

FIG. 5A  FIG. 5B  FIG. 5C
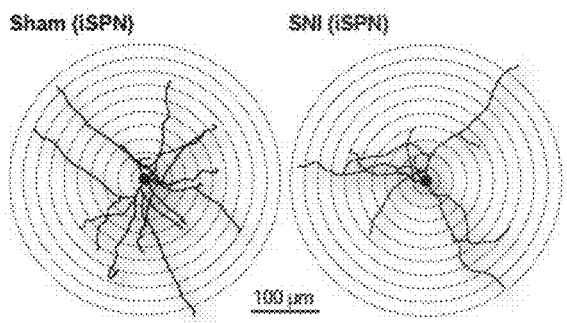 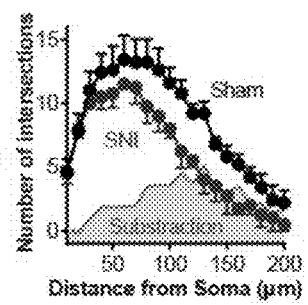 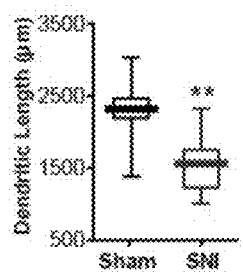
FIG. 5D  FIG. 5E
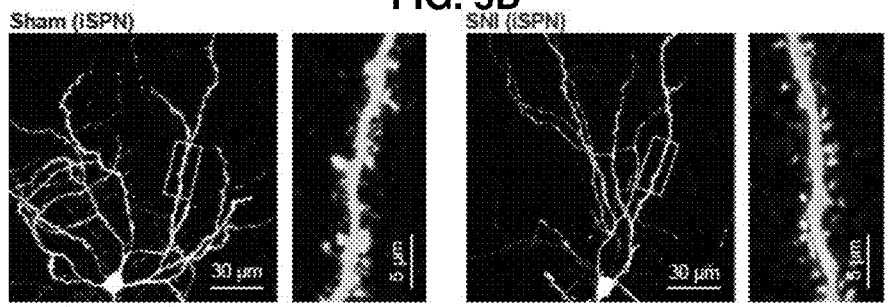 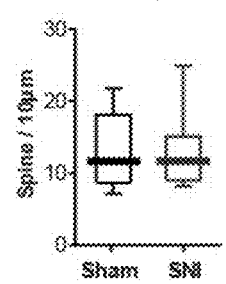
FIG. 5F  FIG. 5G  FIG. 5H
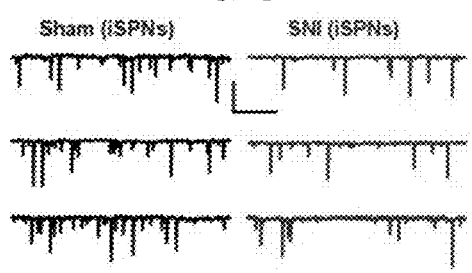 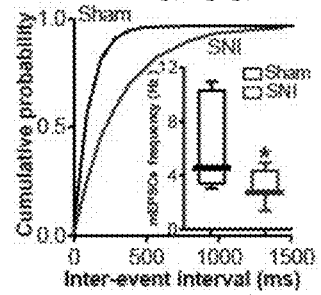 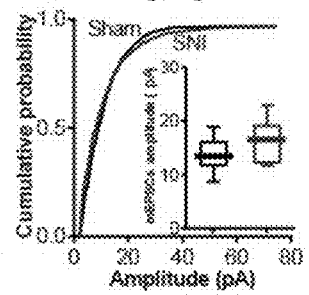

- Sham (Saline)
- SNI/Carrageenan (Saline)
- SNI/Carrageenan (Nap)
- SNI/Carrageenan (Ldopa)
- SNI/Carrageenan (Ldopa+Nap)

SNI

Carrageenan

FIG. 19A
FIG. 19B
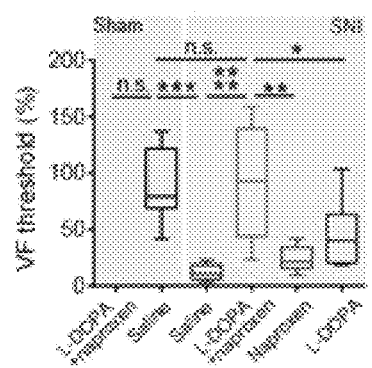
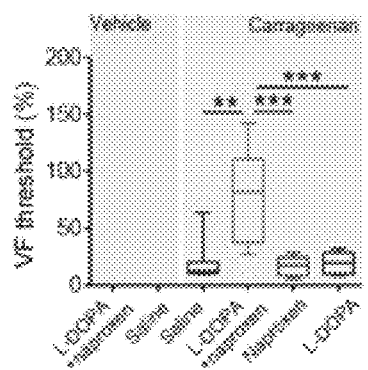
FIG. 19C
FIG. 19D
FIG. 19E
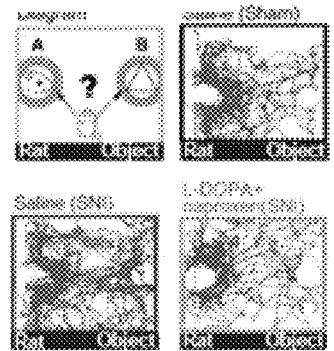
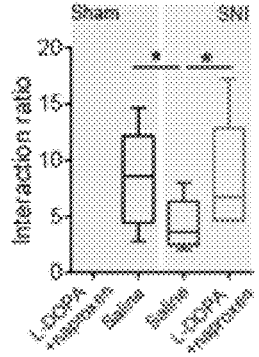
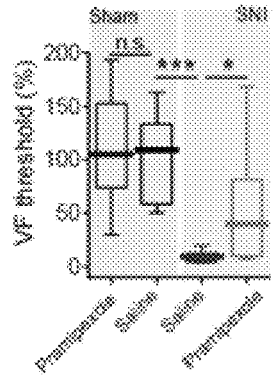

METHODS AND COMPOSITIONS FOR TREATING PAIN

STATEMENT REGARDING FEDERALLY SPONSORED RESEARCH

This invention was made with government support under grant number DE022746 and NS064091 from the National Institutes of Health. The government has certain rights to the invention.

BACKGROUND OF THE INVENTION

Pain is a complex process associated with actual or potential tissue damage, creating an unpleasant sensory and emotional experience. Pain motivates an individual to withdraw from damaging situations, to protect a damaged body part while it heals, and to avoid similar experiences in the future. Most pain is transient and resolves promptly once the stimulus is removed and the body has healed, but some pain can persist despite removal of the stimulus and apparent healing of the body.

Pain conditions can generally be divided into acute pain and chronic pain. Acute pain usually follows non-neural tissue injury (e.g., tissue damage from surgery or inflammation, or migraine) and is usually transient. In contrast, chronic pain persists long after the physiological environment has recovered from damage associated with acute pain. In some cases, chronic pain develops in the absence of any detectable stimulus, damage, or disease. Chronic pain includes neuropathic pain (e.g., post-surgical and post-herpetic neuralgia), chronic inflammatory pain (e.g., arthritis), and pain of unknown origin (e.g., fibromyalgia). The financial burden associated with chronic pain in the United States is estimated to be greater than $500 billion a year, due to decreased productivity and medical expenses. There is a clear need for effective treatments for acute and chronic pain.

There are many drugs that are known to be useful in the treatment or management of pain. Analgesic agents are those that have a direct effect of alleviating pain. One class of analgesics, nonsteroidal anti-inflammatories (NSAIDs), can be used to relieve acute pain and various chronic pain conditions. NSAIDs have limited efficacy in most cases of chronic pain. Additionally, the analgesic effects of NSAIDs are not well characterized with respect to the relationship between acute and chronic pain, and there is a lack of effective treatments for preventing the transition from acute to chronic pain. Therefore, there remains a need to develop effective therapies for the treatment of acute and chronic pain.

SUMMARY OF THE INVENTION

The invention provides compositions, methods, and kits for treating acute pain and chronic pain in a subject (e.g., a mammalian subject, such as a human). The invention also features compositions, methods, and kits for preventing the transition from acute pain to chronic pain in a subject.

In a first aspect, the invention features a pharmaceutical composition having a dopaminergic agent and an analgesic agent in a ratio of about 1:1000 to about 1:2 (e.g., about 1:500 to about 1:5, about 1:250 to about 1:10, or about 1:150 to about 1:15). In some embodiments, the dopaminergic agent is a D1 agonist, a D2 agonist, or a combination thereof. In some embodiments, the D1 agonist is levodopa. Additionally or alternatively, the D2 agonist may be pramipexole or carbidopa. In other embodiments, the dopaminergic agent includes levodopa and carbidopa.

In embodiments of any of the above-described aspects of the invention, the analgesic agent can be paracetamol, an anticonvulsant (e.g., pregabalin, lamotrigine, topiramate, oxcarbazepine, tiagabine, levetiracetam, zonisamide, phenytoin, carbamazepine, gabapentin, or ethosuximide), or a non-steroidal anti-inflammatory drug (NSAID, e.g., naproxen, aceclofenac, acemetacin, acetaminophen, aloxiprin, aspirin, benorilate, bromfenac, celecoxib, deracoxib, diclofenac, diflunisal, ethenzamide, etodolac, etofenamate, etoricoxib, fenbufen, fenoprofen, flufenamic acid, flurbiprofen, lonazolac, lornoxicam, ibuprofen, indomethacin, isoxicam, kebuzone, ketoprofen, ketorolac, licofelone, loxoprofen, lumiracoxib, meclofenamic acid, mefenamic acid, meloxicam, metamizol, mofebutazone, naproxen, nabumetone, niflumic acid, nimesulide, oxaprozin, oxyphenbutazone, parecoxib, phenidone, phenylbutazone, piroxicam, propacetamol, propyphenazone, rofecoxib, salicylamide, sulfinpyrazone, sulindac, suprofen, tiaprofenic acid, tenoxicam, tolmetin, or valdecoxib).

In some embodiments, the composition may have a ratio of levodopa to naproxen of about 1:20. In other embodiments, the ratio of levodopa to naproxen is about 1:100. Alternatively, the composition may have a ratio of pramipexole to naproxen of about 1:150. In certain embodiments, the ratio of carbidopa to levodopa to naproxen is about 1:4:80, respectively.

In embodiments of any of the above-described aspects of the invention, the composition can include the dopaminergic agent in a range of about 0.001 mg to about 1000 mg. Additionally or alternatively, the composition can include the analgesic agents in a range of about 0.01 mg to about 5000 mg.

The compositions of the invention can also include an additional therapeutic agent. In some embodiments, the additional therapeutic agent is a chemotherapeutic agent, such as erlotinib (TARCEVA®), bortezomib (VELCADE®), disulfiram, epigallocatechin gallate, salinosporamide A, carfilzomib, 17-AAG (geldanamycin), radicicol, lactate dehydrogenase A (LDH-A), fulvestrant (FASLODEX®), sunitib (SUTENT®), letrozole (FEMARA®), imatinib mesylate (GLEEVEC®), finasunate (VATALANIB®), oxaliplatin (ELOXATIN®), 5-FU (5-fluorouracil), leucovorin, rapamycin (Sirolimus, RAPAMUNE®), lapatinib (TYKERB®), lonafarnib (SCH 66336), sorafenib (NEXAVAR®), gefitinib (IRESSA®), AG1478, alkylating agents such as thiotepa and CYTOXAN®, cyclophosphamide, alkyl sulfonates (e.g., busulfan, improsulfan and piposulfan; aziridines such as benzodopa, carboquone, meturedopa, and uredopa), ethylenimines and methylamelamines (e.g. altretamine, triethylenemelamine, triethylenephosphoramide, triethylenethiophosphoramide and trimethylomelamine), acetogenins (e.g., bullatacin and bullatacinone), a camptothecin (e.g, topotecan and irinotecan), bryostatin, callystatin CC-1065, adozelesin, carzelesin, bizelesin, cryptophycins, adrenocorticosteroids (e.g. prednisone and prednisolone), cyproterone acetate, 5α-reductases, vorinostat, romidepsin, panobinostat, valproic acid, mocetinostat dolastatin; aldesleukin, talc duocarmycin, eleutherobin pancratistatin, sarcodictyin, spongistatin, nitrogen mustards (e.g., chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard), and nitrosoureas (e.g., carmustine, chlorozotocin, fotemustine, lomustine, nimustine, or ranimnustine).

In some embodiments, the additional therapeutic agent is an anti-inflammatory agent (e.g., acetaminophen, aspirin, celecoxib, cortisone, deracoxib, diflunisal, etoricoxib, fenoprofen, ibuprofen, ketoprofen, lumiracoxib, mefenamic acid, meloxicam, naproxen, parecoxib, phenylbutazone, piroxicam, prednisolone, rofecoxib, sulindac, suprofen, tolmetin, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, 2-(3,5-difluorophenyl)-3-[4-(methylsulfonyl)phenyl]-2-cyclopenten-1-one, anti-tumor necrosis factor (TNF) agents, anti-interleukin (IL) treatment, or anti-CD20).

In certain embodiments, the additional therapeutic agent is an antidepressant (e.g., alaproclate, citalopram, escitalopram, femoxetine, fluoxetine, fluvoxamine, paroxetine, sertraline, zimelidine, adinazolam, amitriptylinoxide, amineptine, amoxapine, atomoxetine, bupropion, butriptyline, demexiptiline, desmethylclomipramine, desipramine, dimetacrine, dothiepin, doxepin, fluacizine, imipramine, imipramine oxide, iprindole, lofepramine, maprotiline, melitracen, metapramine, norclomipramine, nortriptyline (desmethylamitriptyline), noxiptilin, opipramol, perlapine, pizotyline, propizepine, protriptyline, quinupramine, tianeptine, atomoxetine, reboxetine, tomoxetine, viloxazine, amiflamine, bazinaprine, befloxatone, brofaromine, cimoxatone, clorgyline, iproniazid, isocarboxazid, M-3-PPC, moclobemide, pargyline, phenelzine, selegiline, tranylcypromine, vanoxerine, N-methyl-9-oxo-9H-thioxanthene-3-carboxamide 10,10-dioxide (BW-616U), 1-ethylphenoxathiine 10,10-dioxide (BW-1370U87), 4-chloro-2-[(2R)-2-hydroxy-3-morpholin-4-ylpropyl]-5-phenyl-1,2-oxazol-3-one hydrochloride (i.e., CS-722 or RS-722), (5R)-3-[2-((1S)-3-cyano-1-hydroxypropyl)benzothiazol-6-yl]-5-methoxymethyl-2-oxazolidine (E-2011), harmine, harmaline, N-(2-aminoethyl)-5-(m-fluoro-phenyl)-4-thiazolecarboxamide hydrochloride (RO 41-1049), 4-[(7-hydroxy-6,7-dihydro-5H-cyclopenta[d]pyrimidin-4-yl)amino]benzonitrile (RS-8359), (5R)-3-[6-(cyclopropylmethoxy)naphthalen-2-yl]-5-(methoxymethyl)-1,3-oxazolidin-2-one (T-794), 5-(hydroxymethyl)-3-(3-methylphenyl)-1,3-oxazolidin-2-one (toloxatone), N-propargyl-imipramine hydrochloride (K-Y 1349), N-[2-(2-chlorophenoxy)ethyl]cyclopropanamine (LY-51641), N-[2-(2-iodophenoxy)ethyl]cyclopropanamine hydrochloride (LY-121768), N-[2-(2,4-dichlorophenylthio)ethyl]-N-methyl-prop-2-yn-1-amine (M&B 9303), (E)-beta-fluoromethylene-m-tyrosine (MDL 72394), (E)-beta-fluoromethylene-m-tyramine (MDL 72392), 4-(5-chloro-1-benzofuran-2-yl)-1-methylpiperidine (sercloremine), N-methyl-N-propargyl-quinoline hydrochloride (MO 1671), bazinaprine, befloxatone, brofaromine, cimoxatone, moclobemide, adinazolam, amitriptyline/chlordiazepoxide combination, atipamezole, azamianserin, befuraline, bifemelane, binodaline, bipenamol, caroxazone, cericlamine, cianopramine, clemeprol, clovoxamine, dazepinil, deanol, droxidopa, enefexine, estazolam, etoperidone, fengabine, fezolamine, fluotracen, idazoxan, indalpine, indeloxazine, levoprotiline, lithium, litoxetine, medifoxamine, metralindole, mianserin, minaprine, montirelin, nebracetam, nefopam, nialamide, nomifensine, norfluoxetine, orotirelin, oxaflozane, pinazepam, pirlindole, ritanserin, rolipram, setiptiline, sibutramine, sulbutiamine, sulpiride, teniloxazine, thozalinone, thyroliberin, tiflucarbine, tofenacin, tofisopam, toloxatone, trazodone, veralipride, viqualine, or zometapine).

In certain embodiments, the additional agent can also be an antiemetic agent (e.g., dolasetron, granisetron, ondansetron, tropisetron, palonosetron, mirtazapine, domperidone, olanzapine, droperidol, haloperidol, chlorpromazine, prochlorperazine, alisapride, metoclopramide, aprepitant, casopitant, cyclizine, diphenhydramine, dimenhydrinate, doxylamine, meclizine, promethazine, hydroxyzine, cannabis, dronabinol, nabilone, benzodiazepine, and hyoscine).

In some embodiments, the additional agent can be a muscle relaxant, such as benzodiazepine (e.g., diazepam and tetrazepam), nonbenzodiazepines, antispasmodics (e.g., cyclobenzaprine, carisoprodol, chlorzoxazone, meprobamate, methocarbamol, metaxalone, orphenadrine, tizanidine and flupirtine), or antispasticity drugs (e.g., baclofen and dantrolene sodium).

In embodiments of any of the above-described aspects of the invention, the composition can include a pharmaceutically acceptable carrier or excipient. In certain embodiments, the composition is formulated to be administered intravenously, intramuscularly, intravitreally, ocularly, intraocularly, itraorbitally, intradermally, percutaneously, intraarterially, intraperitoneally, intralesionally, intracranially, intraarticularly, intraprostatically, intrapleurally, intratracheally, intrathecally, intranasally, intravaginally, intrarectally, intratumorally, subcutaneously, subconjunctivally, intravesicularly, mucosally, intrapericardially, intraumbilically, orally, topically, by inhalation, by injection, by implantation, by infusion, by continuous infusion, by localized perfusion bathing target cells directly, by catheter, by lavage, in creams, or in lipid compositions. In certain cases, the composition is a liquid. In other cases, the composition is a solid. Additionally or alternatively, the composition can be formulated for sustained release (e.g., from an implanted device).

In an additional aspect, the invention provides a method of reducing pain in a subject (e.g., a mammalian subject, such as a human) by administering to the subject a therapeutically effective amount of a pharmaceutical composition having a dopaminergic agent and an analgesic agent in a ratio of about 1:1000 to about 1:2 for a period of time effective to reduce the pain. In some embodiments of the method, the subject is at risk for experiencing pain. In some cases, the method includes administering a dopaminergic agent that includes a D1 agonist, a D2 agonist, or a combination thereof. In some embodiments, the analgesic agent administered as part of the method can be paracetamol, an anticonvulsant, or a non-steroidal anti-inflammatory drug (NSAID).

In embodiments of any of the above-described methods, the subject may be suffering from acute pain. In some cases, the method of treatment includes administering the dopaminergic and the analgesic agents prior to the onset of acute pain (e.g., no earlier than two months prior to the onset of the acute pain). In other cases, the method of treatment includes administering the dopaminergic and the analgesic agents after the onset of acute pain (e.g., no later than 3 months after the onset of acute pain). In some embodiments, the acute pain is caused by a sports-related injury, a military injury, other physical trauma, a surgical procedure, cancer, infection, inflammation, or childbirth. In some embodiments, the ratio of the dopaminergic agent to the analgesic agent can be between about 1:100 and 1:4 (e.g., between about 1:50 and 1:10, or about 1:20). In some embodiments, the method includes administering levodopa as the D1 agonist.

In some embodiments, the invention provides a method for treating a subject experiencing or acute pain who is additionally at risk for developing chronic pain. In some embodiments, the method prevents the transition from acute pain to chronic pain. In certain cases, the method includes administering a dopaminergic agent that includes both levodopa and carbidopa (e.g., SINEMET®). In some embodiments, the ratio of levodopa to carbidopa to the analgesic agent is about 1:4:80, respectively.

In other embodiments, the invention provides a method for treating a subject experiencing chronic pain. In this embodiment, the dopaminergic agent and the analgesic agent can be administered in a ratio of between about 1:600 and about 1:30, respectively (e.g., about 1:150). In some embodiments, the method includes administering a D2 agonist that includes pramipexole or carbidopa. In some cases, the method of treatment includes administering the dopaminergic and the analgesic agents for a period of time of at least 4 months (e.g., at least 8 months, or at least 12 months).

In embodiments of any of the above-described methods, an additional therapeutic agent (e.g., an antiemetic agent, an antidepressant, an anti-inflammatory agent, a chemotherapeutic, a steroid, or a muscle relaxant) can be administered to a subject experiencing pain. In some embodiments, the additional therapeutic agent is administered at a different time from the dopaminergic agent or the analgesic agent. In other embodiments, the additional therapeutic agent is administered at a different time from the dopaminergic agent or the analgesic agent. In certain cases, the additional therapeutic agent can be administered through a different route from the dopaminergic agent or the analgesic agent. In other cases, additional therapeutic agent can be administered through the same route as the dopaminergic agent or the analgesic agent.

In certain embodiments, the invention provides a method for treating pain in a subject by administering the dopaminergic agent or the analgesic agent in an amount of about 0.01 mg to about 10,000 mg per dose (e.g., about 1 mg to about 5,000 mg per dose, about 5 mg to about 2,000 mg per dose, about 10 mg to about 1,000 mg per dose, about 20 mg to about 500 mg per dose). In certain embodiments, the dopaminergic agent and the analgesic agent are administered at least once or twice per day, week, month, or year.

In embodiments of any of the above-described methods, the dopaminergic agent or the analgesic agent can include a pharmaceutically acceptable carrier or excipient.

In a separate aspect, the invention provides a kit including a pharmaceutical composition comprising a dopaminergic agent and an analgesic agent in a ratio of about 1:1000 to about 1:2 (e.g., about 1:500 to about 1:5, about 1:250 to about 1:10, or about 1:150 to about 1:15). In some embodiments, the kit further includes instructions for administering said composition to a subject at risk of acute or chronic pain, having acute or chronic pain, or at risk of transitioning from acute pain to chronic pain.

As used herein, the term "about" means±10% of the recited value.

As used herein, "acute pain" refers to pain that begins suddenly and can be characterized as being short-lived (e.g., twelve weeks or less). It can result from a direct stimuli, such as soft tissue damage (e.g., caused by surgery, dental work, physical trauma, inflammation, or burn) and can be accompanied by a sharp, stinging pain. Typically, acute pain ceases when the stimulus is removed and resolves as the affected tissue(s) heal.

As used herein, "administer" or "administering" refers to a method of giving a dosage of a composition (e.g., a pharmaceutical composition, e.g., a pharmaceutical composition including a combination of a dopaminergic agent and an analgesic agent) to a subject. The compositions utilized in the methods described herein can be administered, for example, intravenously, intramuscularly, intravitreally (e.g., by intravitreal injection), ocularly (e.g., by eye drop, intraocularly, intraorbitally), intradermally, percutaneously, intraarterially, intraperitoneally, intralesionally, intracranially, intraarticularly, intraprostatically, intrapleurally, intratracheally, intrathecally, intranasally, intravaginally, intrarectally, intratumorally, subcutaneously, subconjunctivally, intravesicularly, mucosally, intrapericardially, intraumbilically, orally, topically, by inhalation, by injection, by implantation, by infusion (e.g., by continuous infusion), by localized perfusion bathing target cells directly, by catheter, by lavage, in creams, or in lipid compositions. The compositions utilized in the methods described herein can also be administered systemically or locally. The method of administration can vary depending on various factors (e.g., the compound or composition being administered and the severity of the condition, disease, or disorder being treated).

As used herein, "agent" refers to a substance, compound (e.g., molecule), supramolecular complex, material, or combination or mixture thereof. A compound can be any agent that can be represented by a chemical formula, chemical structure, or sequence. Examples of agents, include, e.g., small molecules, polypeptides, nucleic acids (e.g., RNAi agents, antisense oligonucleotide, aptamers), lipids, polysaccharides, etc. In general, agents can be obtained using any suitable method known in the art. The ordinary skilled artisan will select an appropriate method based, e.g., on the nature of the agent. An agent can be at least partly purified. An agent can be provided as part of a composition, which can contain, e.g., a counter-ion, aqueous or non-aqueous diluent or carrier, buffer, preservative, or other ingredient, in addition to the agent. An agent can also be provided as a salt, ester, hydrate, or solvate. An agent can be cell-permeable, e.g., within the range of typical agents that are taken up by cells and that act intracellularly, e.g., within mammalian cells, to produce a biological effect.

As used herein, "analgesic agent" refers to an agent that acts to inhibit or suppress pain in a subject. The agent may be a drug that acts on the peripheral and/or central nervous system. Exemplary analgesic agents include non-steroidal anti-inflammatory drugs (NSAIDs, e.g., naproxen), anticonvulsants, and paracetamol (i.e., acetaminophen).

As used herein, "anticonvulsant" refers to an agent that reduces the severity or rate of neuronal firing, thereby promoting antiepileptic effects.

As used herein, "antidepressant" refers to a substance that is used in the treatment of mood disorders, such as those characterized by various manic or depressive affects.

As used herein, "anti-inflammatory agent" refers to an agent that functions to reduce inflammation or swelling. This term encompasses small molecule and biologic drugs, such as methotrexate, and antibodies or fragments thereof that interfere with pro-inflammatory associated pathways (e.g., lymphocyte proliferation and inflammatory cytokine release/activity, e.g., anti-C5 monoclonal antibodies, anti-TNF antibodies, e.g., entanercept or infliximab). Anti-inflammatory agents also include immunosuppressants, including alkylating agents (e.g., cyclophosphamide), antimetabolites (e.g., azathioprine, methotrexate, leflunomide, and mycophenolate mofetil) and macrolides (e.g., cyclosporine and tacrolimus). Assays to determine the anti-inflammatory activity of a given compound are known in the art.

As used herein, "cancer" refers to or describes the physiological condition in mammals that is typically characterized by unregulated cell growth. Included in this definition are benign and malignant cancers, as well as dormant tumors or micrometastases. Examples of cancer include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia, chronic lymphocytic leukemia (CLL), acute lymphoblastic leukemia (ALL), Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome.

As used herein, "chronic pain" refers to persistent pain that is caused by either 1) a pathological condition, such as infection, arthritis, chronic injury (e.g., sprain), cancer, or neuropathic pain, or 2) an acute stimulus after which neurological signaling is compromised by an aberrant healing process. Such pain can persist long after the inciting event. Chronic pain includes, but is not limited to: peripheral neuropathic pain, (e.g., post-herpetic neuralgia, diabetic neuropathic pain, neuropathic cancer pain, failed back-surgery syndrome, trigeminal neuralgia, and phantom limb pain), central neuropathic pain, (e.g., multiple sclerosis related pain, Parkinson disease related pain, post-stroke pain, post-traumatic spinal cord injury pain, and pain from dementia), musculoskeletal pain (e.g., osteoarthritic pain and fibromyalgia syndrome), inflammatory pain (e.g., rheumatoid arthritis and endometriosis), headache (e.g., migraine, cluster headache, tension headache syndrome, facial pain, headache caused by other diseases), visceral pain (e.g., interstitial cystitis, irritable bowel syndrome, and chronic pelvic pain syndrome), and mixed pain, (e.g., lower back pain, neck and shoulder pain, burning mouth syndrome, and complex regional pain syndrome).

As used herein, "chemotherapeutic agent" refers to an anti-cancer drug.

As used herein, "dopaminergic agent" refers to an agent that works to increase dopamine receptor signaling. Dopaminergic agents include direct agonists of dopamine receptors (including the D1, D2, D3, D4, and D5 receptors), as well as an agents that indirectly increases dopaminergic tone. Such agents include dopamine reuptake inhibitors, dopamine releasing agents, and precursors, cofactors, and prodrugs of dopamine or dopaminergic signaling enhancers.

As used herein, "dopamine receptor agonist" refers to an activating ligand of a dopamine receptor. Dopamine receptor agonists can be full or partial agonists and can bind any dopamine receptor type from the D1-like family or the D2-like family.

As used herein, "dopamine releasing compound" refers to an agent that induces the release of dopamine.

As used herein, "dopamine reuptake inhibitor" refers to an agent that functions by blocking the transport of dopamine across physiological compartments (e.g., intracellular vesicles or neuronal synapses). This generally results in the sequestering of dopamine molecules in the vicinity of their receptors and prolonging signaling kinetics.

As used herein, "D1 agonist" refers to a drug which induces signaling through the D1-like family of dopamine receptors (i.e., coupled to the $G_{s\alpha}$ protein). The D1-like family includes receptors D1 and D5.

As used herein, "D2 agonist" refers to a drug which induces signaling through the D2-like family of dopamine receptors (i.e., coupled to the $G_{i\alpha}$ protein). The D2-like family includes receptors D2, D3, and D4.

As used herein, an "effective amount" or "effective dose" of an agent (or composition containing such agent) refers to an amount sufficient to achieve a desired biological and/or pharmacological effect, e.g., when delivered to a cell or organism according to a selected administration form, route, and/or schedule. As will be appreciated by those of ordinary skill in this art, the absolute amount of a particular agent or composition that is effective can vary depending on such factors as the desired biological or pharmacological endpoint, the agent to be delivered, the target tissue, etc. Those of ordinary skill in the art will further understand that an "effective amount" can be contacted with cells or administered to a subject in a single dose or through use of multiple doses.

As used herein, "muscle relaxant" refers to an agent that affects skeletal muscle function and decreases smooth muscle tone.

As used herein, "NSAID" refers to an agent that provides analgesic, antipyretic, and anti-inflammatory effects, including non-selective inhibitors of the enzyme cyclooxygenase. The term also includes free acids, free bases, or pharmaceutically acceptable salts thereof.

As used herein, "package insert" refers to instructions customarily included in commercial packages of medicaments that contain information about the indications, usage, dosage, administration, contraindications, other medicaments to be combined with the packaged product, and/or warnings concerning the use of such medicaments.

As used herein, "paracetamol" refers to the compound known as acetaminophen and includes free acids, free bases, and pharmaceutically acceptable salts thereof.

As used herein, "pharmaceutically acceptable carrier or excipient" refers to a carrier (which term encompasses media, diluents, solvents, vehicles, etc.) or excipient that does not significantly interfere with the biological activity or effectiveness of the active ingredient(s) of a composition and that is not excessively toxic to the host at the concentrations at which it is used or administered.

As used herein, the term "prevent" means to reduce the likelihood of developing a condition, or alternatively, to reduce the severity of a subsequently developed condition. A therapeutic agent can be administered to a subject who is at increased risk of developing a disease or condition relative to a member of the general population in order to prevent the development of, or lessen the severity of, the disease or condition. A therapeutic agent can be administered as a prophylactic, e.g., before development of any symptom or manifestation of a disease or condition.

As used herein, "prophylactic treatment" refers to providing medical and/or surgical management to a subject who has not developed a disease or does not show evidence of a disease in order, e.g., to reduce the likelihood that the disease will occur or to reduce the severity of the disease should it occur.

The subject can have been identified as being at risk of developing the disease (e.g., at increased risk relative to the general population or as having a risk factor that increases the likelihood of developing the disease).

As used herein, "ratio" of one agent to another agent (e.g., the ratio of dopaminergic agent to analgesic agent) refers to the molar ratio of one compound or compounds to another. In cases describing a ratio of a mixture of D1 agonists and/or D2 agonists to analgesic agents, the ratio is taken as the number of moles of the dopaminergic agent relative to the number of moles of the analgesic agent. In cases having two or more dopaminergic agents (e.g., a D1 agonist and a D2 agonist), the ratio is taken as the total number of moles of the dopaminergic agents relative to the number of moles of the analgesic agent.

As used herein, "reducing pain" means decreasing the severity or duration of a subject's sensation of pain.

As used herein, a "subject" is a vertebrate (e.g., a mammal, e.g., a human).

As used herein, "therapeutically effective amount" refers to an amount sufficient to produce a desired result, for example, the reduction or elimination of pain in a subject.

As used herein, "treat", "treating" and similar terms in the context of treating a subject refer to providing medical and/or surgical management of a subject. Treatment can include, but is not limited to, administering an agent or composition (e.g., a pharmaceutical composition) to a subject. Treatment is typically undertaken in an effort to alter the course of a disease (which term is used to indicate any disease, disorder, syndrome or undesirable condition warranting or potentially warranting therapy) in a manner beneficial to the subject. The effect of treatment can include reversing, alleviating, reducing severity of, curing, inhibiting the progression of, and/or reducing the likelihood of recurrence of the disease or one or more symptoms or manifestations of the disease. A therapeutic agent can be administered to a subject who has had a disease but no longer shows evidence of the disease (e.g., a subject that is disease-free, but continues to experience pain). The agent can be administered, e.g., to reduce the likelihood of recurrence of evident disease.

BRIEF DESCRIPTION OF THE DRAWINGS

The application file contains at least one drawing executed in color. Copies of this patent or patent application with color drawings will be provided by the Office upon request and payment of the necessary fee.

FIGS. 1A-1H are photographs identifying the direct and indirect spiny projection neurons (SPNs) in nucleus accumbens (NAc) shell slices. FIG. 1A is a brightfield image showing a sagittal NAc shell slice obtained from a bacterial artificial chromosome (BAC) transgenic mouse (D, dorsal; V, ventral; R, rostral; C, caudal). FIG. 1B is a fluorescent photomicrograph identifying iSPNs (enchanced green fluorescent protein (eGFP)-positive, green) and direct pathway SPNs (dSPNs, Td tomato-positive, red) within individual NAc slices. FIG. 1C and FIG. 1F are fluorescent photomicrographs each showing an indirect pathway SPN (iSPN) filled with biocytin. FIG. 1D is a fluorescent photomicrograph showing the eGFP-positive iSPNs. FIG. 1E is a fluorescent photomicrograph showing the overlap of FIG. 1C and FIG. 1D. FIG. 1G is a fluorescent photomicrograph showing the Td tomato positive dSPNs. FIG. 1H is a fluorescent photomicrograph showing the overlap of FIG. 1F and FIG. 1G.

FIGS. 2A-2H are graphs showing the differences in electrophysiological properties in iSPNs and dSPNs between sham and naïve mice. FIG. 2A is a graph showing Von Frey (VF) withdrawal thresholds on BAC or wildtype (WT) mice receiving a spared nerve injury (SNI) procedure at pre-surgery (Day 0) and post-surgery (Day 5). FIG. 2B is a graph showing Von Frey (VF) withdrawal thresholds on BAC or wildtype (WT) mice receiving a sham procedure at pre-surgery (Day 0) and post-surgery (Day 5). FIG. 2C is a graph showing spike number in iSPNs between sham and naïve groups (n=11 for each group, p>0.05, two-way ANOVA). FIG. 2D is a graph showing spike number in dSPNs between sham and naïve groups (n=11 for each group, p>0.05, two-way ANOVA). FIG. 2E is a graph showing the first spike latency of iSPNs between sham and naïve mice (p>0.05, two-way ANOVA). FIG. 2F is a graph showing the first spike latency of dSPNs between sham and naïve mice (p>0.05, two-way ANOVA). FIG. 2G is a graph showing the rheobase current between sham and naïve mice either in iSPNs or dSPNs (p>0.05, Mann-Whitney Utest). FIG. 2H is a graph showing the input resistance between sham and naïve mice either in iSPNs or dSPNs (p>0.05, Mann-Whitney Utest).

FIG. 3A is a representative reconstruction of the dSPNs by Sholl analysis from sham and SNI animals. FIG. 3B is a graph showing the number of intersections as a function of the distance from the soma between SNI and sham animals (n=10 in each group, p>0.05, two-way ANOVA). FIG. 3C is a graph showing the total length of dendrites in SNA and Sham animals (n=10 in each group, p>0.05, Mann-Whitney U test). FIG. 3D is a set of photomicrographs of dSPNs dendrites/spines from sham and SNI animals. FIG. 3E is a graph showing the spine density of dSPNs in SNI and Sham animals (n=10 in each group, p>0.05, Mann-Whitney Utest). FIG. 3F is a representative set of miniature excitatory post-synaptic currents (mEPSC) recordings obtained in dSPNs (calibration bar: 20 pA, 400 ms). FIG. 3G is a set of graphs showing the mEPSC frequency of dSPNs of SNA and Sham animals (n=7-8 in each group, p>0.05, Kolmogorov-Smirnov test for Cumulative probability histograms and Mann-Whitney Utest for box plots). FIG. 3H is a set of graphs showing the mEPSCs amplitude of dSPNs of SNA and Sham animals (n=7-8 in each group, p>0.05, Kolmogorov-Smirnov test for Cumulative probability histograms and Mann-Whitney U test for box plots).

FIG. 4A is a fluorescent photomicrograph of an individual NAc shell slice of a BAC transgenic mouse, which identifies iSPNs (eGFP-positive, green) and dSPNs (Td tomato-positive, red). FIG. 4B is a fluorescent photomicrograph of an individual NAc shell slice of a BAC transgenic mouse, which identifies a biocytin-filled iSPN (white arrow, CY5-Biocytin is in blue). FIG. 4C is a fluorescent photomicrograph of an individual NAc shell slice of a BAC transgenic mouse, which identifies a biocytin-filled dSPN (white arrow, CY5-Biocytin is in blue). FIG. 4D is a set of graphs showing representative excitabilities of contralateral iSPNs (calibration bars: 20 mV, 200 ms; current injections: −40, 20, 60 and 100 pA). FIG. 4E is a graph showing intrinsic iSPN excitability in acute slices of NAc shell of sham and SNI animals in response to depolarizing current injections in contralateral NAc. FIG. 4F is a set of graphs showing representative excitabilities of ipsilateral iSPNs (calibration bars: 20 mV, 200 ms; current injections: −40, 20, 60 and 100 pA). FIG. 4G is a graph showing intrinsic iSPN excitability in acute slices of NAc shell of sham and SNI animals in response to depolarizing current injections in ipsilateral NAc. FIG. 4H is a set of graphs showing representative excitabilities of contralateral dSPNs (calibration bars: 20 mV, 200 ms; current injections: −40, 100, 200 and 240 pA). FIG. 4I is a graph showing intrinsic dSPN excitability in acute slices of NAc shell of sham and SNI animals in response to depolarizing current injections in contralateral NAc. FIG. 4J is a set of graphs showing representative excitabilities of ipsilateral dSPNs (calibration bars: 20 mV, 200 ms; current injections: −40, 100, 200 and 240 pA). FIG. 4K is a graph showing intrinsic dSPN excitability in acute slices of NAc shell of sham and SNI animals in response to depolarizing current injections in ipsilateral NAc. FIG. 4L is a graph showing first-spike latency differences between sham and SNI animals in iSPNs ($p<0.0001$, two-way ANOVA). FIG. 4M is a graph showing first-spike latency differences between sham and SNI animals in dSPNs ($p<0.0001$, two-way ANOVA). FIG. 4N is a graph showing rheobase current differences between sham and SNI animals in iSPNs and dSPNs ($p<0.001$, Mann-Whitney Utest). FIG. 4O is a graph comparing the input resistance in iSPNs and dSPNs in sham and SNI animals ($p<0.01$ for iSPNs and $p>0.05$ for dSPNs, Mann-Whitney Utest).

FIG. 5A is a representative three-dimensional Sholl analysis of reconstructed iSPNs from sham and SNI animals. FIG. 5B is a graph showing the number of intersections as a function of the distance from the soma between SNI and sham animals ($n=10$ in each group, $p<0.0001$, two-way ANOVA). FIG. 5C is a graph showing the total length of dendrites in SNA and Sham animals ($n=10$ in each group, $p<0.01$, Mann-Whitney U test). FIG. 5D is a set of photomicrographs of iSPNs dendrites/spines from sham and SNI animals. FIG. 5E is a graph showing the spine density of iSPNs (45-105 µm from soma) in SNI and Sham animals ($p>0.05$, Mann-Whitney Utest). FIG. 5F is a representative set of mEPSC recordings obtained in iSPNs (calibration bar: 20 pA, 400 ms). FIG. 5G is a set of graphs showing the mEPSCs frequency of iSPNs of SNA and Sham animals ($n=7$ in each group, $p<0.05$, Kolmogorov-Smirnov test for Cumulative probability histograms and Mann-Whitney Utest for box plots). FIG. 5H is a set of graphs showing the mEPSC amplitude of iSPNs of SNA and Sham animals ($n=7$ in each group, $p>0.05$, Kolmogorov-Smirnov test for Cumulative probability histograms and Mann-Whitney Utest for box plots).

FIG. 19A is a graph showing the effects of naproxen, levodopa, and their co-treatment on VF thresholds in SNI rats relative to sham controls (n=8-9). FIG. 19B is a graph showing the effects of naproxen, levodopa, and their co-treatment on VF thresholds in carrageenan-treated rats relative to vehicle controls (n=8). FIG. 19C is a set of representative tracks of the space explored by rats in each group during the sociability test. FIG. 19D is a graph showing the effects of levodopa and naproxen co-treatment on the interaction ratio of SNI rats compared with sham controls. FIG. 19E is a graph showing the effect of pramipexole on the VF threshold in SNI rats, in comparison to sham controls.

DETAILED DESCRIPTION OF THE INVENTION

Figure 6A:
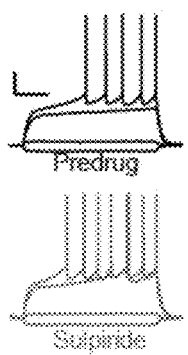
FIG. 6A is a set of graphs showing representative excitabilities of iSPNs before and after administering D2 receptor agonist sulpiride (5 µM) in sham animals (calibration bars: 20 mV, 200 ms; current injections: −40, 20, 60 and 100 pA).

The invention features combinations of one or more analgesic agents and one or more dopaminergic agents and associated methods useful for the treatment or prevention of pain. Such combinations potentiate analgesia to 1) alleviate acute pain, 2) prevent the transition from acute pain to chronic pain, and 3) manage chronic pain.

I have discovered that the induction of neuropathic pain is associated with distinct physiological adaptations of the nucleus accumbens (NAc). One adaptation is an increase in dopamine transporter (DAT) expression, which is accompanied by a drop in extracellular dopamine levels. The other is an increase in the intrinsic excitability of indirect pathway spiny projection neurons (iSPNs) and a reduction in their dendritic surface area and glutamatergic innervation. As iSPNs express D2 dopamine receptors that diminish cellular excitability, peripheral nerve injury can induce an up-regulation of DAT expression in ventral tegmental area (VTA) dopamine neurons, diminishing extracellular dopamine concentration and thus disinhibiting iSPNs. The resulting tonic elevation in iSPN excitability can then trigger homeostatic mechanisms resulting in dendritic shrinkage and the loss of excitatory synaptic input. Thus, while not being bound by theory, dopaminergic agents may work by normalizing iSPN excitability and blunting changes in dendritic morphology and synaptic connectivity, resulting in alleviation of pain.

Furthermore, I have discovered that the pain-alleviating effects of dopaminergic agents synergize with analgesic agents, such as naproxen. This synergy could stem from the involvement of both central and peripheral mechanisms in the induction of the chronic state. Specifically, while not being bound by theory, it is possible that analgesic agents alleviate SNI-triggered suppression of VTA activity enough to allow levodopa to normalize NAc dopamine levels.

Thus, the invention features methods of treating or preventing pain (e.g., acute pain, chronic pain, or the transition between acute and chronic pain) by administering dopaminergic agents in conjunction with analgesic agents (e.g., as part of the same composition or different compositions, or at the same time or separate times) in a low ratio, respectively. The amount of dopaminergic agent in a composition can be minimized to avoid well-characterized adverse side effects associated with many dopaminergic agents. The molar ratio of dopaminergic agent to analgesic agent can be from about 1:1000 to about 1:2, from about 1:500 to about 1:5, from about 1:250 to about 1:10, or from about 1:150 to about 1:15. Specifically, the molar ratio can be about 1:150, 1:140, 1:130, 1:120, 1:110, 1:100, 1:90, 1:80, 1:70, 1:60, 1:50, 1:40, 1:30, 1:25, 1:20, 1:15, 1:10, 1:8, 1:6, 1:5, or 1:4, dopaminergic agent to analgesic agent. The specific molar ratio will depend on factors such as whether the pain is acute or chronic and whether the dopaminergic drug is a D1 agonist or a D2 agonist, as described herein.

Methods of Treatment

The invention features methods of treating a subject experiencing or expecting to experience pain. A subject in need of a treatment for pain can be administered a dopaminergic agent, e.g., a dopamine receptor agonist or precursors thereof (e.g., 2-OH-NPA, 6-Br-APB, 7-OH-DPAT, 8-OH-PBZI, A-412997, A-68930, A-77636, A-86929, ABT-670, ABT-727, amantadine, aplindore, apomorphine, aripiprazole, apomorphine, bifeprunox, BP-897, bromocriptine, cabergoline, carbidopa, carmoxirole, ciladopa, cloazapine, CY-208243, dihydroergocryptine, dihydrexidine, dinapsoline, dinoxyline, dizocilpine, dopamine, doxanthrine, epicriptine, etilevodopa, fenoldopam, flibanserin, ketamine, L-phenylalanine, L-tyrosine, levodopa, lisuride, lysergic acid diethylamide, melevodopa, memantine, metoclopramide, modafinil, pardoprunox, PD-128907, PD-168007, PF-219061, pergolide, phencyclidine, piribedil, pramipexole, propylnorpomorphine, pukateine, quinagolide, quinelorane, quinpirole, RDS-127, rimantadine, Ro10-5824, ropinirole, rotigotine, roxindole, salvinorin A, SKF-23390, SKF-38393, SKF-77434, SKF-81297, SKF-82958, SKF-83959, SKF-89145, sumanirole, terguride, UH-232, umespirone, or WAY-100635).

Dopamine receptor agonists and precursors thereof that preferentially act on D1 receptors include, e.g., levodopa, SKF-38393, SKF-23390, and clozapine. Dopamine receptor agonists and precursors thereof that preferentially act on D2 receptors include pramipexole, bromocriptine, carbidopa, pergolid, lisuride, guinpirole, metoclopramide, and carmoxirole.

Additionally, dopamine reuptake inhibitors (e.g., buprio-pion (WELLBUTRIN®), bicifadine, or GBR12909) can be administered as the dopaminergic agent of the invention. Other dopamine reuptake inhibitors are known in the art or can be identified by standard pharmacological in-vitro protocols, e.g., as disclosed in Janowsky et al., 1986, *J Neurochem*, 46 1272-1276. Any other agent or combination that works by directly or indirectly enhancing dopamine signaling can also be used as part of the invention (e.g., dopamine releasing compounds, monoamine oxidase inhibitors, e.g., rasagiline or selegiline).

Analgesic agents that can be administered as part of the invention include non-steroidal anti-inflammatory drugs (NSAIDs, e.g., COX-1 or COX-2 inhibitors, e.g., naproxen, aceclofenac, acemetacin, acetaminophen, aloxiprin, aspirin, benorilate, bromfenac, celecoxib, deracoxib, diclofenac, diflunisal, ethenzamide, etodolac, etofenamate, etoricoxib, fenbufen, fenoprofen, flufenamic acid, flurbiprofen, lonazolac, lornoxicam, ibuprofen, indomethacin, isoxicam, kebuzone, ketoprofen, ketorolac, licofelone, loxoprofen, lumiracoxib, meclofenamic acid, mefenamic acid, meloxicam, metamizol, mofebutazone, naproxen, nabumetone, niflumic acid, nimesulide, oxaprozin, oxyphenbutazone, parecoxib, phenidone, phenylbutazone, piroxicam, propacetamol, propyphenazone, rofecoxib, salicylamide, sulfinpyrazone, sulindac, suprofen, tiaprofenic acid, tenoxicam, tolmetin, or valdecoxib).

Alternatively, the analgesic agent of the invention can be an anticonvulsant (e.g., pregabalin, lamotrigine, topiramate, oxcarbazepine, tiagabine, levetiracetam, zonisamide, phenytoin, carbamazepine, gabapentin, or ethosuximide).

Other analgesic agents, such as paracetamol (i.e., acetaminophen), are known in the art and can be used as part of the methods of the invention.

To treat pain in a subject, dopaminergic agents and analgesic agents described above can be administered in a molar ratio from about 1:1000 to about 1:2, respectively, depending on the type of pain. Specifically, a combination of D1 agonists and analgesic agents can be used to treat acute pain, while a combination of D2 agonists and analgesic agents can be used to treat chronic pain, as described below.

Acute Pain

To treat or prevent acute pain in a subject, a combination of a dopaminergic agent and an analgesic agent can be administered at a molar ratio from about 1:100 to 1:4, respectively (e.g., about 1:100, 1:90, 1:80, 1:70, 1:60, 1:50, 1:40, 1:30, 1:20, 1:10, 1:8, 1:6, 1:5, or 1:4). The dopaminergic agent can be a D1 agonist (e.g., levodopa), and the analgesic agent can be an NSAID (e.g., naproxen).

A subject who is likely to experience acute pain (e.g., prior to childbirth, prior to surgical procedures, prior to military operations, prior to athletic activities, or any circumstance in which a subject is at risk of or expecting to experience pain) can be administered one or more doses of a combination of a D1 agonist and an analgesic agent prior to the onset of the acute pain (e.g., within 1 minute, 5 minutes, 15 minutes, 30 minutes, 1 hour, 2 hours, 4 hours, 6 hours, 12 hours, 18 hours, 1 day, 2 days, 3 days, 4 days, 5 days, 6 days, 1 week, 2 weeks, 3 weeks, 4 weeks, 6 weeks, or 8 weeks prior to the onset of acute pain).

A subject who is currently experiencing acute pain (e.g., as a result of a sports-related injury, a military injury, other physical trauma, surgical procedure, cancer, infection, inflammation, or any stimuli resulting in an injury sufficient to stimulate a wound-healing response in the subject) can be administered a combination of a D1 agonist and an analgesic agent shortly after (within, e.g., 1 minute, 5 minutes, 15 minutes, 30 minutes, 1 hour, 2 hours, 4 hours, 6 hours, 12 hours, 18 hours, 1 day, 2 days, 3 days, 4 days, 5 days, 6 days, 1 week, 2 weeks, 3 weeks, 4 weeks, 6 weeks, 8 weeks, 10 weeks, or 3 months) the onset of the acute pain. The administration can begin soon after the onset of acute pain to increase the degree and the likelihood of alleviation of acute pain.

Chronic Pain

The invention also features methods to treat or prevent chronic pain in a subject. A subject suffering from chronic pain can be administered a D2 agonist and an analgesic agent (e.g., a combination of pramipexole and naproxen, or a combination of carbidopa and naproxen). The combination of D2 agonist and analgesic agent can be administered at a molar ratio from about 1:600 to 1:30, respectively (e.g., about 1:600, 1:500, 1:400, 1:300, 1200, 1:150, 1:100, 1:90, 1:80, 1:70, 1:60, 1:50, 1:40, or 1:30). Administrations can occur continuously, as required, over a period of time (e.g., about four months, five months, six months, seven months, eight months, nine months, ten months, eleven months, twelve months, or longer).

Chronic pain conditions include, e.g., peripheral neuropathic pain, (e.g., post-herpetic neuralgia, diabetic neuropathic pain, neuropathic cancer pain, failed back-surgery syndrome, trigeminal neuralgia, and phantom limb pain), central neuropathic pain, (e.g., multiple sclerosis related pain, Parkinson disease related pain, post-stroke pain, post-traumatic spinal cord injury pain, and pain from dementia), musculoskeletal pain (e.g., osteoarthritic pain and fibromyalgia syndrome), inflammatory pain (e.g., rheumatoid arthritis and endometriosis), headache (e.g., migraine, cluster headache, tension headache syndrome, facial pain, headache caused by other diseases), visceral pain (e.g., interstitial cystitis, irritable bowel syndrome, and chronic pelvic pain syndrome), and mixed pain (e.g., lower back pain, neck and shoulder pain, burning mouth syndrome, and complex regional pain syndrome).

In addition to treating acute pain and chronic pain, methods of the invention also feature preventing the transition from acute pain to chronic pain. A subject suffering from acute pain can be administered a D2 agonist, a D1 agonist, and an analgesic agent (e.g., a combination of carbidopa, levodopa, and an NSAID, e.g., SINEMET® and naproxen) to prevent the transition to chronic pain. The combination can be administered at a molar ratio of about 1:4:80, respectively, in one or more doses.

Conditions in which acute pain can develop into chronic pain are known in the art and include, e.g., nerve damage caused by trauma or disease, which can develop into chronic neuropathic pain. Chronic neuropathic pain conditions include, e.g., peripheral neuropathy, diabetic neuropathy, post-herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Cancer-related acute pain can also be associated with a risk of developing chronic pain. Such conditions include, e.g., tumor-related bone pain, headache, facial pain, visceral pain, post-chemotherapy syndrome, chronic post-surgical syndrome, and post-radiation syndrome. Acute back pain (e.g., resulting from herniated or ruptured intervertebral disks, or abnormalities of the lumbar facet joints, sacroiliac joints, paraspinal muscles or the posterior longitudinal ligament) can also lead to chronic back pain. Infection-related acute pain associated with inflammation can lead to chronic inflammatory pain (e.g., pain associated with arthritis, rheumatoid arthritis, ankylosing spondylitis, inflammatory bowel disease, Crohn's disease, ulcerative colitis, or post-herpetic neuralgia).

The particular combinations of dopaminergic agents and analgesic agents described above can be administered according to the methods described below.

Dosing and Administration

Methods of the invention include various dosing regimens. In general, a dopaminergic agent and an analgesic agent can be administered simultaneously at any of the molar ratios described herein (e.g., as part of a single composition). Alternatively, a dopaminergic agent can be administered separately from the analgesic agent, as long as they are administered at a molar ratio from about 1:1000 to 1:2.

The dose of each component of the invention can vary depending on factors such as the type of pain being treated (e.g., acute pain, chronic pain, or transition from acute to chronic pain). A therapeutically effective dose of an analgesic agent, a dopaminergic agent, or a composition comprising a dopaminergic and an analgesic agent can be within a range of about 1 µg/kg to about 500 mg/kg body weight, about 2 µg/kg to about 100 mg/kg, about 5 µg/kg to about 10 mg/kg, about 0.01 mg/kg to about 25 mg/kg, about 0.1 mg/kg to about 20 mg/kg body weight, about 1 mg/kg to about 10 mg/kg, about 1 mg/kg to about 3 mg/kg, about 3 mg/kg to about 5 mg/kg, about 5 mg/kg to about 10 mg/kg, and can be administered once or more per day, week, month, or other time interval.

In particular, a therapeutically effective dose of an analgesic agent could be from about 1.0 mg/kg to about 30 mg/kg, and a therapeutically effective dose of a dopaminergic agent (e.g., a D1 agonist or a D2 agonist, or both a D1 and a D2 agonist) could be from about 50 µg/kg to about 2.0 mg/kg. In a treatment including both a D1 agonist and a D2 agonist (e.g., levodopa and carbidopa), effective doses can be, e.g., about 1.5 mg/kg and 0.375 mg/kg, respectively.

A single dose including both a dopaminergic agent and an analgesic agent can be administered, or multiple doses can be administered. Each of the multiple doses can include an analgesic agent, a dopaminergic agent, or a composition having both a dopaminergic agent and an analgesic agent. Those of ordinary skill in the art will appreciate that appropriate doses in any particular circumstance depend upon the potency of the agent(s) utilized, and can optionally be tailored to the particular recipient. The specific dose level for a subject can depend upon a variety of factors including the activity of the specific agent(s) employed, severity of the disease or disorder, the age, body weight, general health of the subject, etc. Conventional dosage regimens for oral administration of treatments for acute pain are described by Sachs et al., 2005, *American Family Physician* 1; 71, 913-918.

Methods of the invention include any suitable route of administration. The dopaminergic and analgesic agents can be administered, e.g., intravenously, intramuscularly, intravitreally (e.g., by intravitreal injection), ocularly (e.g., by eye drop, intraocularly, intraorbitally), intradermally, percutaneously, intraarterially, intraperitoneally, intralesionally, intracranially, intraarticularly, intraprostatically, intrapleurally, intratracheally, intrathecally, intranasally, intravaginally, intrarectally, intratumorally, subcutaneously, subconjunctivally, intravesicularly, mucosally, intrapericardially, intraumbilically, orally, topically, by inhalation, by injection, by implantation, by infusion (e.g., by continuous infusion), by localized perfusion bathing target cells directly, by catheter, by lavage, in creams, or in lipid compositions.

The invention also features formulations of the dopaminergic agents and the analgesic agents that can be administered according to the routes of administration described above.

Formulations

Dopaminergic agents and analgesic agents can be admixed as part of the same formulation. Alternatively, they can be separate formulations, which can each be administered separately, or through the same route, as described above. Each agent can be formulated as either a liquid or a solid for any suitable route of administration, such as those described above. For oral administration, agents can be formulated by combining the active compounds with pharmaceutically acceptable carriers well known in the art. Such carriers enable the agents of the invention to be formulated as capsules, tablets, pills, dragees, liquids, gels, syrups, slurries, suspensions and the like, for oral ingestion by a subject to be treated. Suitable excipients for oral dosage forms are, e.g., fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). Disintegrating agents can be added, such as the cross linked polyvinyl pyrrolidone, agar, or alginic acid or a salt thereof such as sodium alginate. Oral formulations can also be formulated in saline or buffers for neutralizing internal acid conditions or can be administered without any carriers. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include capsules (e.g., push-fit capsules) made of gelatin, as well as soft, sealed capsules made of gelatin and a plasticizer, such as glycerol or sorbitol. The capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Microspheres formulated for oral administration can also be used. Such microspheres have been well defined in the art. Formulations for oral delivery can incorporate agents to improve stability in the gastrointestinal tract and/or to enhance absorption.

Preparations for parenteral administration include sterile aqueous or non-aqueous solutions, suspensions, and emulsions. Aqueous carriers include water, alcoholic/aqueous solutions, emulsions or suspensions, including saline and buffered media, e.g., sodium chloride solution, Ringer's dextrose, dextrose and sodium chloride, lactated Ringer's. Examples of non-aqueous solvents are propylene glycol, polyethylene glycol, vegetable oils such as olive oil, and injectable organic esters such as ethyl oleate, fixed oils, polyethylene glycols, glycerine, propylene glycol or other synthetic solvents, preservatives (e.g., antibacterial agents such as benzyl alcohol or methyl parabens), antioxidants (e.g., ascorbic acid and sodium bisulfite), chelating agents (e.g., ethylenediaminetetraacetic acid), buffers (e.g., acetates, citrates and phosphates), and agents for the adjustment of tonicity (e.g., sodium chloride and dextrose). The pH can be adjusted with acids or bases, such as hydrochloric acid or sodium hydroxide. Such parenteral preparations can be enclosed in ampoules, disposable syringes or multiple dose vials made of glass or plastic.

For administration by inhalation, pharmaceutical compositions can be delivered in the form of an aerosol spray from a pressured container or dispenser which contains a suitable propellant (e.g., carbon dioxide, a fluorocarbon, or a nebulizer). Liquid or dry aerosol (e.g., dry powders, large porous particles, etc.) can be used. The invention includes delivery of agents using a nasal spray or other forms of nasal administration (e.g., for delivery to the central nervous system (e.g., the brain)). Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers.

For topical application, the combination of dopaminergic agent and analgesic agent can be formulated in a suitable ointment, lotion, gel, or cream containing the active agents suspended or dissolved in one or more pharmaceutically acceptable carriers. The agents can be formulated according to conventional pharmaceutical practice (see, e.g., Remington: The Science and Practice of Pharmacy, 20th edition, 2000, ed. A. R. Gennaro, Lippincott Williams & Wikins, Philadelphia, and Encyclopedia of Pharmaceutical Technology, eds. J. Swarbrick and J. C. Boylan, 1988-1999, Marcel Dekker, New York). The agents can be formulated using any dermatologically acceptable carrier. Exemplary carriers include a solid carrier, such as alumina, clay, microcrystalline cellulose, silica, or talc; and/or a liquid carrier, such as an alcohol, a glycol, or a water-alcohol/glycol blend. The agents can also be administered in liposomal formulations that allow therapeutic agents to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; 8,822,537, and PCT Publication No. WO 96/40061. Examples of other appropriate vehicles are described in U.S. Pat. Nos. 4,877,805, 8,822,537, and EP Publication No. 0586106A1. Suitable vehicles of the invention can also include mineral oil, petrolatum, polydecene, stearic acid, isopropyl myristate, polyoxyl 40 stearate, stearyl alcohol, or vegetable oil. Compositions for topical application of analgesic drugs are described in U.S. Pat. No. 5,589,480, included by reference herein.

Formulations can further include a skin penetrating enhancer, such as those described in "Percutaneous Penetration enhancers", (eds. Smith E W and Maibach H I. CRC Press 1995). Exemplary skin penetrating enhancers include alkyl (N,N-disubstituted amino alkanoate) esters, such as dodecyl 2-(N,N dimethylamino) propionate (DDAIP), which is described in U.S. Pat. Nos. 6,083,996 and 6,118,020, which are both incorporated herein by reference; a water-dispersible acid polymer, such as a polyacrylic acid polymer, a carbomer (e.g., Carbopol™ or Carbopol 940P™, available from B. F. Goodrich Company (Akron, Ohio)), copolymers of polyacrylic acid (e.g., Pemulen™ from B. F. Goodrich Company or Polycarbophil™ from A. H. Robbins, Richmond, Va.; a polysaccharide gum, such as agar gum, alginate, carrageenan gum, ghatti gum, karaya gum, kadaya gum, rhamsan gum, xanthan gum, and galactomannan gum (e.g., guar gum, carob gum, and locust bean gum), as well as other gums known in the art (see for instance, Industrial Gums: Polysaccharides & Their Derivatives, Whistler R. L., BeMiller J. N. (eds.), 3rd Ed. Academic Press (1992) and Davidson, R. L., Handbook of Water-Soluble Gums & Resins, McGraw-Hill, Inc., N.Y. (1980)); or combinations thereof.

Dopaminergic agents or analgesic agents can also be formulated for sustained release, such as from an implanted construct or device. In, e.g., orthopedic replacement operations, a sustained release of pain-treating agents into the local or systemic environment is useful to minimize acute pain and the transition to chronic pain. These agents can be formulated as encapsulants within a porous or degradable matrix, such as a biocompatible polymeric matrix. Materials for sustained release of dopaminergic agents from implantable devices are provided by U.S. Pat. No. 8,852,623, incorporated herein by reference. In general, the size, shape, and/or chemistry of a polymeric material, matrix, or formulation can be appropriately selected to result in release in therapeutically useful amounts over a useful time period, in the tissue into the polymeric material, matrix, or formulation is implanted or administered.

A wide variety of biocompatible materials can be utilized as a sustained release carrier to provide the sustained release of dopaminergic agents and analgesic agents, alone or in combination with one or more biologically active agents, as described herein. Any pharmaceutically acceptable biocompatible polymer known to those skilled in the art can be utilized. The biocompatible controlled release material can degrade in vivo within about one year (e.g., within about 2 to 3 months). Specifically, the controlled release material can degrade significantly within one to three months, with at least 50% of the material degrading into non-toxic residues, which are removed by the body, and 100% of the compound of the invention being released within a time period within about two weeks (e.g., within about 2 days to about 7 days). A degradable controlled release material can degrade by hydrolysis, either by surface erosion or bulk erosion, so that release is not only sustained but also provides desirable release rates. The pharmacokinetic release profile of these formulations can be first order, zero order, bi- or multiphasic, to provide the desired reversible local anesthetic effect over the desired time period.

The biodegradable material can be prepared by any method known to those skilled in the art. For example, where the polymeric material includes a copolymer of lactic and glycolic acid, this copolymer can be prepared by the procedure set forth in U.S. Pat. No. 4,293,539, incorporated herein by reference. Alternatively, copolymers of lactic and glycolic acid can be prepared by any other procedure known to those skilled in the art. Other useful polymers include polylactides, polyglycolides, polyanhydrides, polyorthoesters, polycaprolactones, polyphosphazenes, polyphosphoesters, polysaccharides, proteinaceous polymers, soluble derivatives of polysaccharides, soluble derivatives of proteinaceous polymers, polypeptides, polyesters, and polyorthoesters or mixtures and blends of any of these.

Methods for formulating liposomal compositions of analgesic drugs are described in U.S. Pat. No. 5,451,408, included by reference herein, and such methods can be used for formulations of the either the dopaminergic agents, the analgesic agents, or both, in the prescribed ratio.

Compositions

In addition to methods of treating and preventing acute and chronic pain, the invention features pharmaceutical compositions having a combination of a dopaminergic agent and an analgesic agent in any of the molar ratios according to the methods described above (e.g., from about 1:1000 to about 1:2, e.g., from about 1:500 to about 1:5, from about 1:250 to about 1:10, from about 1:150 to about 1:15, respectively). Additionally, the compositions can contain any of the dopaminergic agents or analgesic agents in the molar ratios described in the methods (e.g., a D1 agonist and an analgesic agent in a molar ratio of about, e.g., 1:100 or 1:20, respectively; a D2 agonist and an analgesic in a molar ratio of about 1:150, respectively; or a D2 agonist, a D1 agonist, and an analgesic agent in a molar ratio of about 1:4:80, respectively). Compositions of the invention include any formulation (e.g., as described above) that contains the dopaminergic agent admixed with the analgesic agent.

The amount of dopaminergic agent in each unit dose of the composition can be in the range of about 1.0 µg to about 1000 mg (e.g., about 1.0 µg, 2.0 µg, 5.0 µg, 10 µg, 25 µg, 50 µg, 100 µg, 250 µg, 500 µg, 1.0 mg, 2.5 µg, 5.0 mg, 10 mg, 25 µg, 50 mg, 100 mg, 250 mg, 500 mg, or 1000 mg). The amount of analgesic agent in each unit dose of the composition can be in the range of about 0.01 mg to about 5000 mg (e.g., about 10 µg, 25 µg, 50 µg, 100 µg, 250 µg, 500 µg, 1.0 mg, 2.5 µg, 5.0 mg, 10 mg, 25 µg, 50 mg, 100 mg, 250 mg, 500 mg, 1000 mg, 2000 mg, 2500 mg, 3000 mg, 4000 mg, 5000 mg).

Kits

The invention further provides kits that can have one or more containers (e.g., bottles, blister packs, vials, ampoules) containing unit dosage forms comprising the dopaminergic agents and analgesic agents of the invention (e.g., the compositions described above), and, optionally, one or more additional pharmaceutical agents. Each agent (e.g., the dopaminergic agent or the analgesic agent) can be contained in separate containers or in the same container. Associated with such container(s) (e.g., enclosed in a package together with the container) can be a notice in the form prescribed by a governmental agency regulating the manufacture, use or sale of pharmaceutical products (e.g., the US Food & Drug Administration or European Medicines Agency), which reflects approval by the agency of manufacture of use or sale for human administration for treatment of acute or chronic pain. The notice can describe, e.g., doses, routes and/or methods of administration, approved indications, methods of monitoring for therapeutically effective levels, and/or other information of use to a medical practitioner and/or patient.

Additional Agents

The compositions, methods, and kits of the invention can additionally include one or more other therapeutic agents for the prevention or treatment of secondary conditions. Additional agents can be administered at the same time or at a different time (e.g., by the same route of administration or by a different route of administration, or as part of the same or different compositions) as the dopaminergic and analgesic combination. Agents useful in combination with the compositions and methods of the invention include antiemetic agents, antidepressants, anti-inflammatory agents, chemotherapeutics, steroids, and muscle relaxants.

Antiemetic agents that can be used as part of the present invention include dolasetron, granisetron, ondansetron, tropisetron, palonosetron, mirtazapine, domperidone, olanzapine, droperidol, haloperidol, chlorpromazine, prochlorperazine, alisapride, metoclopramide, aprepitant, casopitant, cyclizine, diphenhydramine, dimenhydrinate, doxylamine, meclizine, promethazine, hydroxyzine, cannabis, dronabinol, nabilone, benzodiazepine, and hyoscine.

Antidepressants that can be used as part of the invention include alaproclate, citalopram, escitalopram, femoxetine, fluoxetine, fluvoxamine, paroxetine, sertraline, zimelidine, adinazolam, amitriptylinoxide, amineptine, amoxapine, atomoxetine, bupropion, butriptyline, demexiptiline, desmethylclomipramine, desipramine, dimetacrine, dothiepin, doxepin, fluacizine, imipramine, imipramine oxide, iprindole, lofepramine, maprotiline, melitracen, metapramine, norclomipramine, nortriptyline (desmethylamitriptyline), noxiptilin, opipramol, perlapine, pizotyline, propizepine, protriptyline, quinupramine, tianeptine, atomoxetine, reboxetine, tomoxetine, viloxazine, amiflamine, bazinaprine, befloxatone, brofaromine, cimoxatone, clorgyline, iproniazid, isocarboxazid, M-3-PPC, moclobemide, pargyline, phenelzine, selegiline, tranylcypromine, vanoxerine, N-methyl-9-oxo-9H-thioxanthene-3-carboxamide 10,10-dioxide (BW-616U), 1-ethylphenoxathiine 10,10-dioxide (BW-1370U87), 4-chloro-2-[(2R)-2-hydroxy-3-morpholin-4-ylpropyl]-5-phenyl-1,2-oxazol-3-one hydrochloride (i.e., CS-722 or RS-722), (5R)-3-[2-((IS)-3-cyano-1-hydroxypropyl)benzothiazol-6-yl]-5-methoxymethyl-2-oxazolidine (E-2011), harmine, harmaline, N-(2-aminoethyl)-5-(m-fluoro-phenyl)-4-thiazolecarboxamide hydrochloride (RO 41-1049), 4-[(7-hydroxy-6,7-dihydro-5H-cyclopenta[d]pyrimidin-4-yl)amino]benzonitrile (RS-8359), (5R)-3-[6-(cyclopropylmethoxy)naphthalen-2-yl]-5-(methoxymethyl)-1, 3-oxazolidin-2-one (T-794), 5-(hydroxymethyl)-3-(3-methylphenyl)-1,3-oxazolidin-2-one (toloxatone), N-propargyl-imipramine hydrochloride (K-Y 1349), N-[2-(2-chlorophenoxy)ethyl]cyclopropanamine (LY-51641), N-[2-(2-iodophenoxy)ethyl]cyclopropanamine hydrochloride (LY-121768), N-[2-(2,4-dichlorophenylthio)ethyl]-N-methyl-prop-2-yn-1-amine (M&B 9303), (E)-beta-fluoromethylene-m-tyrosine (MDL 72394), (E)-beta-fluoromethylene-m-tyramine (MDL 72392), 4-(5-chloro-1-benzofuran-2-yl)-1-methylpiperidine (sercloremine), N-methyl-N-propargyl-quinoline hydrochloride (MO 1671), bazinaprine, befloxatone, brofaromine, cimoxatone, moclobemide, adinazolam, amitriptyline/chlordiazepoxide combination, atipamezole, azamianserin, befuraline, bifemelane, binodaline, bipenamol, caroxazone, cericlamine, cianopramine, clemeprol, clovoxamine, dazepinil, deanol, droxidopa, enefexine, estazolam, etoperidone, fengabine, fezolamine, fluotracen, idazoxan, indalpine, indeloxazine, levoprotiline, lithium, litoxetine, medifoxamine, metralindole, mianserin, minaprine, montirelin, nebracetam, nefopam, nialamide, nomifensine, norfluoxetine, orotirelin, oxaflozane, pinazepam, pirlindole, ritanserin, rolipram, setiptiline, sibutramine, sulbutiamine, sulpiride, teniloxazine, thozalinone, thyroliberin, tiflucarbine, tofenacin, tofisopam, toloxatone, trazodone, veralipride, viqualine, and zometapine.

Anti-inflammatory agents that can be used as part of the invention include small-molecule drugs such as acetaminophen, aspirin, celecoxib, cortisone, deracoxib, diflunisal, etoricoxib, fenoprofen, ibuprofen, ketoprofen, lumiracoxib, mefenamic acid, meloxicam, naproxen, parecoxib, phenylbutazone, piroxicam, prednisolone, rofecoxib, sulindac, suprofen, tolmetin, valdecoxib, 4-(4-cyclohexyl-2-methyl-oxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, and 2-(3,5-difluorophenyl)-3-[4-(methylsulfonyl)phenyl]-2-cyclopenten-1-one.

Anti-inflammatory biologic agents can also be used as part of the invention and include, but are not limited to, anti-tumor necrosis factor (TNF) agents (e.g. adalimumab, infliximab, or etanercept), anti-interleukin (IL) treatment (e.g. anti-IL-1α, IL-1β, IL-1RA), and anti-CD20 (e.g. tiuximab).

Chemotherapeutic agents that can be used as part of the invention include erlotinib (TARCEVA®), bortezomib (VELCADE®), disulfiram, epigallocatechin gallate, salinosporamide A, carfilzomib, 17-AAG (geldanamycin), radicicol, lactate dehydrogenase A (LDH-A), fulvestrant (FASLODEX®), sunitib (SUTENT®), letrozole (FEMARA®), imatinib mesylate (GLEEVEC®), finasunate (VATALANIB®), oxaliplatin (ELOXATIN®), 5-FU (5-fluorouracil), leucovorin, rapamycin (Sirolimus, RAPAMUNE®), lapatinib (TYKERB®), lonafamib (SCH 66336), sorafenib (NEXAVAR®), gefitinib (IRESSA®), AG1478, alkylating agents such as thiotepa and CYTOXAN®, cyclosphosphamide, alkyl sulfonates (e.g., busulfan, improsulfan and piposulfan; aziridines such as benzodopa, carboquone, meturedopa, and uredopa), ethylenimines and methylamelamines (e.g. altretamine, triethylenemelamine, triethylenephosphoramide, triethylenethiophosphoramide and trimethylomelamine), acetogenins (e.g., bullatacin and bullatacinone), a camptothecin (e.g, topotecan and irinotecan), bryostatin, callystatin CC-1065, adozelesin, carzelesin, bizelesin, cryptophycins, adrenocorticosteroids (e.g. prednisone and prednisolone), cyproterone acetate, 5α-reductases, vorinostat, romidepsin, panobinostat, valproic acid, mocetinostat dolastatin; aldesleukin, talc duocarmycin, eleutherobin pancratistatin, sarcodictyin, spongistatin, nitrogen mustards (e.g., chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard), and nitrosoureas (e.g., carmustine, chlorozotocin, fotemustine, lomustine, nimustine, or ranimnustine).

Muscle relaxants that can be used as part of the invention include benzodiazepines (e.g., diazepam and tetrazepam), nonbenzodiazepines antispasmodics (e.g., cyclobenzaprine, carisoprodol, chlorzoxazone, meprobamate, methocarbamol, metaxalone, orphenadrine, tizanidine and flupirtine), and antispasticity drugs (e.g., baclofen and dantrolene sodium).

Assessment of Pain

To measure the efficacy of any of the methods, compositions, or kits of the invention, a measurement index can be used. Indices that are useful in the methods, compositions, and kits of the invention for the measurement of pain include the Pain Descriptor Scale (PDS), the Visual Analog Scale (VAS), the Verbal Descriptor Scales (VDS), the Numeric Pain Intensity Scale (NPIS), the Neuropathic Pain Scale (NPS), the Neuropathic Pain Symptom Inventory (NPSI), the Present Pain Inventory (PPI), the Geriatric Pain Measure (GPM), the McGill Pain Questionnaire (MPQ), mean pain intensity (Descriptor Differential Scale), numeric pain scale (NPS) global evaluation score (GES) the Short-Form McGill Pain Questionnaire, the Minnesota Multiphasic Personality Inventory, the Pain Profile and Multidimensional Pain Inventory, the Child Heath Questionnaire, and the Child Assessment Questionnaire.

EXAMPLES

The following examples are put forth so as to provide those of ordinary skill in the art with a description of how the compositions and methods claimed herein can be performed, made, and evaluated, and are intended to be purely exemplary of the invention and are not intended to limit the scope of what the inventor regards as his or her invention.

Example 1. Methods for Testing the Efficacy of Compositions for Treating and Preventing Pain Forebrain limbic circuitry has been implicated in the expression of chronic pain (Raz, 2009, *Perspectives in biology and medicine* 52, 555-565). The nucleus accumbens (NAc) is a key component of this circuitry (Bromberg et al, 2010, *Neuron* 68, 815-834). Human studies suggest that neurons in the NAc encode pain salience and value for pain relief, and the strength of its functional connectivity with the medial prefrontal cortex is predictive of the transition to chronic pain (Baliki et al, 2010, *Neuron* 66, 149-160). Animal studies of persistent pain also have implicated the NAc. Infusion of dopaminergic agonists into the NAc ameliorates the tactile allodynia in a rodent neuropathic pain model (Sarkis et al, 2011, *Eqp. Neurol.* 228, 19-29). The NAc shell also appears to be important in signaling value for pain relief (Baliki et al, 2013, *The Journal of Neuroscience* 33, 16383-93). Given the well-established linkage of the NAc circuitry to networks controlling stimulus salience and affective value, these findings suggest that the NAc might be critical for the establishment of chronic neuropathic pain. In other brain areas linked to chronic pain, induction of persistent pain is correlated with functional and morphological reorganization (Metz et al, 2009, *PNAS* 106, 2423-2428). Accordingly, this example provides various methods to test physiological mechanisms of pain-relieving therapies.

Animals

Electrophysiology studies were carried out in 8-week-old male C57BL6 wild-type (WT) and bacterial artificial chromosome (BAC)-transgenic mice (D1 receptor-Td Tomato and D2 receptor-enhanced Green Fluorescent Protein (eGFP)). Animals were housed with food and water available ad libitum and with a 12 h light/dark cycle (7 A.M.-7 P.M.). Tactile threshold of each animal was measured on Day 0 pre-surgery and Day 5 post-surgery before sacrificing the animal. In another set of behavioral experiments, the effects of oral drug treatment on tactile sensitivity and sociability were assessed on 8-week-old Sprague-Dawley rats. Rats were housed with littermates under the same conditions as above. In these groups of animals, tactile thresholds were measured before surgical manipulation and then again on assigned date post-surgery. The adult male SD rats were also used for in-vivo brain microdialysis and DAT quantification using western blot experiments. All studies were approved by the Animal Care and Use Committee of Northwestern University or by the Local Animal Care Committee (Sun Yat-sen University) and were carried out in accordance with the guidelines of the National Institutes of Health on animal care and with the ethical guidelines for investigation of experimental pain in conscious animal.

Neuropathic Pain Model: Spared Nerve Injury (SNI)

The SNI model has been described previously (Zimmerman, 1983, Pain 16, 109-110). Mice or rats were anesthetized with isoflurane 1.5-2% and a mixture of 30% $N_2O$ and 70% $O_2$. The left hind leg sciatic nerve was exposed at the level of the trifurcation into the sural, tibial, and common peroneal nerves. The tibial and common peroneal nerves were tightly ligated and severed, leaving the sural nerve intact. Animals in the sham surgery group had their sciatic nerve exposed as in the SNI procedure, but they received no further manipulations.

Tactile Sensitivity

Paw withdrawal thresholds to Von Frey filament stimulation (VF) were used to assess mechanical sensitivity of the hind-paws. Animals were placed in a Plexiglas box with a wire grid floor and allowed to habituate for 15-30 min. Then, filaments of various forces (Stoelting) were applied to the plantar surface of each hind-paw. Filaments were applied in a descending and ascending pattern, determined by the response of the animal. Each filament was applied for a maximum of 2 seconds, and paw withdrawal in response to the filament was considered a positive response. Fifty percent thresholds were calculated according to Chaplan et al, 1994, *Journal of neuroscience methods* 53, 55-63. The injured paw withdrawal thresholds of all SNI animals were significantly decreased compared with the pre-surgery level and Sham animals.

Electrophysiology i) Brain Slices Preparation.

Sagittal brain slices of the NAc shell (250 μm) were obtained from BAC D1 and D2 receptor transgenic mice. The mice were anesthetized with ketamine/xylazine and perfused transcardially with ice-cold artificial CSF (aCSF), containing in mM: 125 NaCl, 2.5 KCl, 1.25 $NaH_2PO_4$, 2.0 $CaCl_2$, 1.0 $MgCl_2$, 25 $NaHCO_3$, and 25 glucose, saturated with 95% $O_2$ and 5% $CO_2$. Brains were rapidly removed and sliced in oxygenated, ice-cold, aCSF using a VT1200S vibratome (Leica Microsystems). Slices were obtained from medial shell and did not contain any dorsal striatal tissue (0.44-0.52 mm lateral, FIG. 1A) (Paxinos and Franklin, 2007, Elsevier Academic Press); they were transferred to a holding chamber and incubated in aCSF at 35° C. for 30 min, and then stored at room temperature until used for patch clamp recordings (1-5 h). The extracellular aCSF was saturated with 95% $O_2$/5% $CO_2$ at all times to maintain oxygenation and a pH ~7.4.

ii) Visualized Whole-Cell Patch-Clamp Recording Ex-Vivo.

Slices were visualized using an upright microscope (Nikon) equipped with infrared differential interference contrast (IR-DIC) optics and with a Hitachi CCD camera (KP-M2RN). The recording chamber was superfused with carbogen-saturated aCSF at a flow rate of 2-3 ml min$^{-1}$. Picrotoxin (100 μM) was added to block GABAA receptor-mediated IPSCs. A combination of CNQX (10 μM) and D-AP5 (50 μM) was used to block glutamatergic transmission during action potential recording. Recordings were made at 32-34% C using a Multiclamp 700B amplifier (Molecular Devices). Patch electrodes were pulled on a Flaming-Brown horizontal puller (P-97; Sutter Instruments) from filamented, thick-wall borosilicate-glass (1.5 mm O.D., Sutter Instruments). Pipette resistance was typically ~3-5 MO when filled with an internal solution consisting of: 140 mM $KMeSO_4$, 10 mM KCl, 10 mM HEPES, 2 mM $Mg_2ATP$, 0.4 mM NaGTP, 10 mM sodium phosphocreatine and 0.2% (wt/vol) biocytin; pH 7.25-7.30; 300 mOsm. Data were acquired using a Digidata 1322A interface (Molecular Devices) and were collected using pClamp9 (Molecular Devices). Current clamp data were filtered at 10 KHz and voltage clamp data were filtered at 5 KHz using the built-in filter of the amplifier. In each NAc shell slice, neuronal somatic eGFP or Td-Tomato expression was verified routinely in cell-attach to confirm cell identity before breaking into whole-cell mode. Current clamp recordings were performed to quantify firing properties. Input resistance (Ri) was monitored on-line with a 40 pA, 150 ms current injections given before every 800 ms current injection stimulus. Only cells with a stable Ri (A<20% for the duration of the recording) were kept for analysis. Spikes were evoked using current step injections (800 ms duration at 0.1 Hz, −160 to +320 pA range with 20 pA steps). Rheobase current was defined as the first current step capable of eliciting an action potential. Miniature excitatory post-synaptic currents (mEPSCs) were measured in voltage clamp at a holding potential of ~80 mV and in the presence of 500 nM tetrodotoxin (TTX, to block voltage-gated sodium currents). Frequency and amplitude distributions of mEPSCs were analyzed using MiniAnalysis program 6.0.3 (Synaptosoft) over a 5 minutes time interval.

iii) Drugs and Drug Application.

Sulpiride and Bicifadine were obtained from Tocris. CBR12909 was obtained from Sigma-Aldrich. Drugs were bath applied for at least 15 min to establish equilibrium in the tissue.

Confocal Imaging/Anatomical Reconstruction

For anatomical reconstruction, 0.2% biocytin was included in the internal solution and neurons were recorded in whole-cell mode for at least 30 min. Slices were fixed in 4% paraformaldehyde overnight. After several washes, slices were reacted for 6 hours with streptavidin-Cy5 (Invitrogen, 1200) in 0.5% Triton-X, 1% BSA, 10% normal goat serum (in PBS) at 20-22° C. in the dark. Sections were then washed and coverslipped with prolong gold antifade reagent (Invitrogen). A cell was rejected if the soma was not intact or any dye was seen in neighboring cells. For anatomical reconstruction, serial optical sections (Z-stacks) were acquired using a 0.415×0.415×0.5 μm$^3$ voxel size on a laser-scanning confocal microscope (LSM 510; Olympus) with a 60×/1 NA oil-immersion objective (Zeiss). Z-series of the same cell were combined using Fiji Software (VIAS; Mt. Sinai Computational Neurobiology and Imaging Center), and subsequently reconstructed and analyzed using the Neurolucida/Neuroexplorer suite (MicroBrightField). No correction was applied for tissue shrinkage. For spine counting, serial Z-stacks were acquired using a 0.069×0.069×0.1 µm$^3$ voxel size. Images were deconvoluted using Autoquata (MediaCybernetics). Counting was performed on 45- to 105-µm long segments of the principal dendrite. Spines were counted only if they had both a punctuate head and visible neck.

In Vivo Brain Microdialysis

Under chloral hydrate anesthesia (0.4 g/kg, i.p.), animals were implanted bilaterally in the NAc (AP+1.7 mm; ML±0.8 mm; DV −7 mm according to the atlas of Paxinos and Watson (2005, Elsevier Academic Press) with dialysis guide cannulas (10 mm, MD-2250, O-ring, BASi, USA). The guide cannulas were fixed to the skull with stainless steel screws and dental acrylic. In vivo brain microdialysis was performed in freely moving rats at assigned time points to examine the concentration of dopamine (DA) in NAc. The 320 µm diameter dialysis probes, which have 2 mm-long functional membranes, were inserted into the NAc one day before the experiment to minimize damage-induced dopamine release. On the day of the experiment, dialysis buffer (124 mM NaCl, 3.3 mM KCl, 1.2 mM $KH_2PO_4$, 26 mM $NaHCO_s$, 2.5 mM $CaCl_2$ and 2.4 mM $MgSO_4$, pH 7.4) was perfused through the dialysis probe (1 µL/min) via syringe pump (MD-1001, BASi) for 90 min before sample collection. In the next 1 hour, 10 µl dialysis samples were collected every 30 min and dialysate DA was immediately measured by HPLC with electrochemical detection system (BASi). DA was separated using a BASi C18 column (5 µm, 100 mm×1 mm) and oxidized/reduced using a BASi LC Epsilon electrochemical detector which contained a BASi 6 mm Glassy carbon electrode and three silver/silver chloride reference electrodes (MF-2078, BASi). The DA mobile phase consists of 3.28 mM sodium heptanesulfonate, 0.16 mM EDTA, 100.81 mM sodium acetate, and 93 mM citric acid, PH 3.7. The area under the curve of the DA peak was measured using BASi ChromGraph Performance-Verified Software (Ver. 2.5×). DA values were quantified with an external calibration curve (50-2000 µg/ml).

Western Blot Analysis

5 Sham and 5 SNI animals were decapitated at post-surgery Day 5, and the brains were removed and sliced. NAc tissue was homogenized and equal amounts of proteins were separated by gel electrophoresis (SDS-PAGE) and transferred to PVDF membrane. The membrane was blocked and then probed with primary antibody against DAT (1:200, Millipore) and β-actin (1:1000, Cell Signalling Technology) overnight at 4° C. Membranes were then incubated with an HRP-conjugated secondary antibody (CST) at room temperature. Protein bands were detected by ECL detection reagent (RPN2232; GE Healthcare) and captured on an autoradiography film (Kodak). Integrated optical density was determined using Image-Pro Plus software 6.0 (Media Cybernetics). Standard curves were constructed to verify that we operated within the linear range of the detection method.

Systemic Drug Administration

All the drugs were dissolved in saline and were administered at the following doses: saline (2 ml/kg), naproxen (30 mg/kg), levodopa (1.5 mg/kg), or a combination of either levodopa with naproxen or levodopa with naproxen and carbidopa (0.375 mg/kg). Individual drug doses did not change regardless of whether administered alone or in combination. All the drugs were obtained from Sigma-Aldrich. Drugs were given by gavage twice daily and 8 hours apart, beginning 2 hours before the surgery (sham/SNI) or carrageenan injection and continuing for the duration of entire experiment. VF threshold measurements were taken at one and two days prior to surgery or injection to verify stable baselines. For the SNI/Sham animal, VF threshold measurements were taken on Day 3 post-surgery and repeated every 3-4 days in order to track the effects of the medication on pain behavior; for the carrageenan model, VF thresholds were measured once a day for one week post carrageenan injection.

Sociability Test

Figure 8A:
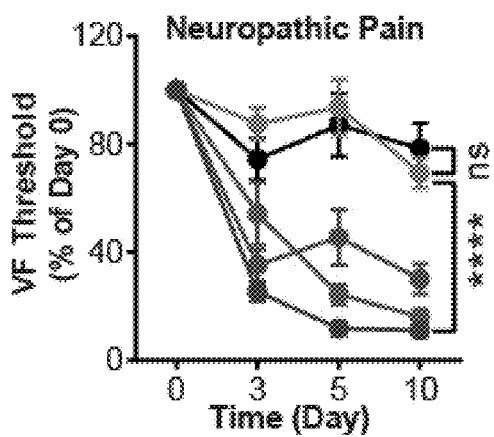
FIG. 8A is a graph showing the effect of co-administering levodopa and naproxen on SNI-induced tactile allodynia, in comparison to the drugs individually ($n=8$-9 in each group, $p<0.0001$, two-way ANOVA followed by Tukey's multiple comparisons test).
Figure 8B:
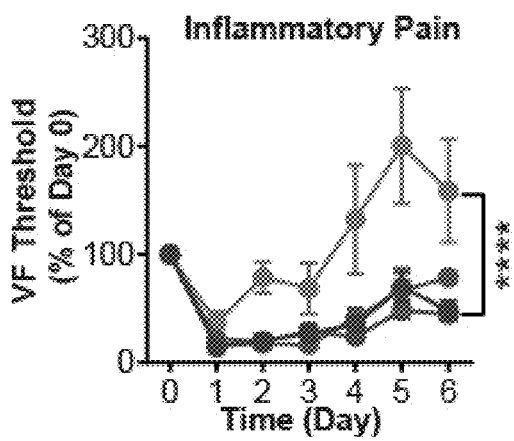
FIG. 8B is a graph showing the effect of co-administering levodopa and naproxen on carrageenan-induced tactile allodynia, in comparison to the drugs individually ($n=8$ in each group, $p<0.0001$, two-way ANOVA followed by Tukey's multiple comparisons test).
Figure 8C:
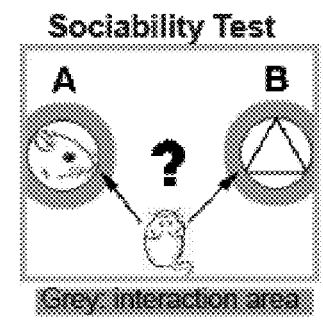
FIG. 8C is a diagram illustrating the sociability test.

The Sociability Test, adapted from Yang et al, 2007 Fronteirs in behavioral neuroscience 1, 1 . . . , assessed an animal's preference for social versus non-social interaction. Briefly, the apparatus consisted of an opaque Plexiglas box with two wired cups (A and B) placed directly across from one another; these cups allowed the experimental animals to approach and interact with confined conspecifics/objects without direct contact. The box was placed in a quiet room, and a camera was fixed over the box to record behavior. The animals received 10-minute habituation (both cups are empty) on Day 12 post-surgery, and twenty-four hours later sociability test was performed after another 10-minute habituation. In each test, a male rat was placed in the box and exposed to a juvenile female rat (Cup A) and an object (Cup B) for 10 min (FIG. 8C). The object used was approximately the same size and the same color as the conspecific to control for any different visual cues. Using ANY-maze (version 4.98) visual tracking software, we measured the time rats spent interacting with each cup (interaction is defined as rat's head being within the zone surrounding each cup), and the ratio of exploration time for Cup A over that for Cup B was calculated. The box, cups, and objects were cleaned with soapy water and bleach between each animal's tests. Three groups were compared: Sham with saline (2 ml/kg) treatment, SNI with saline (2 ml/kg) treatment, and SNI with levodopa (1.5 mg/kg) and naproxen (30 mg/kg) co-administration treatment. Drugs were administered by gavage twice daily, which began in the morning of surgery and were continued until testing day.

Statistics

Data analyses were done with ClampFit 9 (Molecular Devices), MiniAnalysis 6.0.3 (Synaptosoft), and Prism 5 (GraphPad). Intensity-response and morphological Sholl analysis data are presented as mean±SEM and the curves were analyzed with two-way repeated measures ANOVA. Group main effect between treatment groups is reported. Box plots are used for graphic representation: the central line represents the median, the edges represent the interquartile ranges, and the whiskers represent the overall distribution. Normal distributions were not assumed regardless of sample size or variance. Pairwise comparisons for unrelated samples were performed using a Mann-Whitney Utest. The data of behavioral test and microdialysis are presented as mean±SEM and ordinary one-way ANOVA or two-way ANOVA was used with appropriate post-hoc tests as indicated. Kolmogorov-Smirnov tests were used for cumulative distribution analysis of miniature EPSCs. P value of <0.05 was considered significant.

Example 2. Peripheral Neuropathic Injury Selectively Increased ISPNs Excitability Because NAc dSPNs and iSPNs are differentially linked to behavioral activation, which is clearly altered in chronic pain states (Alba et al, 2013, Biological Psychiatry 73, 54-62), it was important to distinguish between them in our assays. To do so, our studies took advantage of transgenic mice in which dSPNs and iSPNs expressed red and green fluorescent proteins, respectively (FIG. 4A and FIG. 1B). These transgenic mice did not differ from wild-type in their response to SNI (FIGS. 2A-2B). To minimize experimental variability, one dSPN and one iSPN were sampled from the same brain slice (FIGS. 4B-4C and FIGS. 1C-1H). Five days after the SNI (or sham) surgery, mice were tested for tactile allodynia and sacrificed to obtain sagittal brain slices containing the ipsilateral and contralateral NAc. SPNs in the NAc shell were visually identified by their fluorescence and then whole cell patch clamp recordings were made. In shell iSPNs from SNI mice, intrinsic excitability assessed by intrasomatic current injection was significantly increased both ipsilateral and contralateral to the nerve injury (FIGS. 4D-4G). Additionally, rheobase current and first spike latency decreased, whereas input resistance increased (FIGS. 4L, 4N, 4O). In contrast, SNI had no effect on neighboring dSPNs (FIGS. 4H-4K, FIGS. 4M-4O). Because of the similarity of responses in the ipsilateral and contralateral shell, they were pooled in further experiments.

Example 3. SNI Induced Shortening of ISPNs Dendrites

To determine if there were morphological changes accompanying the elevation in intrinsic excitability, iSPNs of the NAc shell were filled with biocytin and then reconstructed. This analysis revealed profound changes in iSPNs dendrites following SNI (FIG. 5). To quantify these changes, dendritic trees were subjected to a Sholl branching analysis and to dendritic path length measurements. The Sholl branching analysis revealed that iSPN dendrites from SNI mice had reduced branching than sham (FIGS. 5A, 5B). Moreover, total dendritic length was reduced (FIG. 5C). In contrast, neighboring dSPNs dendrites were unaffected (FIGS. 3A-3E). Although dendritic branching and length were reduced in iSPNs following SNI, spine density was unchanged (FIGS. 5D-E). Nevertheless, the reduction in dendritic length should lead to a reduction in the total number of excitatory glutamatergic synapses. To test this prediction, glutamatergic miniature excitatory post-synaptic currents (mEPSCs) were measured in SPNs from SNI and sham mice. As expected, mEPSC frequency was reduced selectively in iSPNs from SNI mice (FIGS. 5F-5H, FIGS. 3F-3H).

Figure 6B:
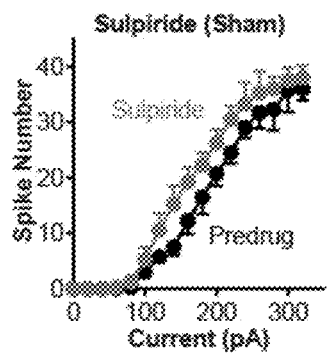
FIG. 6B is a graph showing the iSPN spike number as a function of current before and after administering sulpiride in sham animals.
Figure 6C:
FIG. 6C is a set of graphs showing representative excitabilities of iSPNs before and after administering sulpiride in SNI animals (calibration bars: 20 mV, 200 ms; current injections: −40, 20, 60 and 100 pA).
Figure 6D:
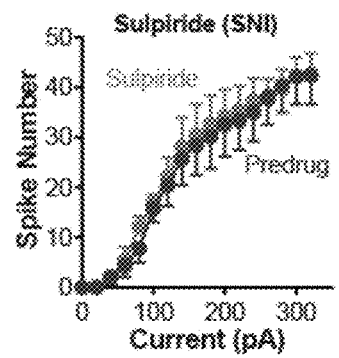
FIG. 6D is a graph showing the iSPN spike number as a function of current before and after administering sulpiride in SNI animals.

Example 4. SNI-Induced Adaptations in NAc were Attributable to Diminished Extracellular Dopamine D2 dopamine receptor signaling decreased the excitability of iSPNs (19). Because striatal D2 receptors exist primarily in a high-affinity state (Missale et al, 1998, *Physiological reviews* 78, 189-225), they are capable of detecting changes in tonic dopamine release by pacemaking VTA dopaminergic neurons (Li et al, 2012, *Journal of neurophysiology* 107, 2808-20). In contrast, D1 dopamine receptors are found primarily in a low affinity binding state in situ, and are less influenced by basal dopamine levels. Thus, one possible explanation for the selective effects of SNI on iSPNs is that tonic dopamine level in the shell of the NAc was reduced in SNI, leading to increased excitability and homeostatic down-regulation in dendritic surface area and synaptic connectivity. In keeping with this hypothesis, when a D2 receptor antagonist (sulpiride, 5 µM) was applied to brain slices from sham mice it increased the excitability of iSPNs (FIGS. 6A-6B), demonstrating that a tonic activation of D2 receptors is present in control conditions. However, when the same experiment was done in slices from SNI mice, there was no detectable change in iSPNs excitability (FIGS. 6C-6D), suggesting that the tonic modulation was diminished or absent.

Figure 6E:
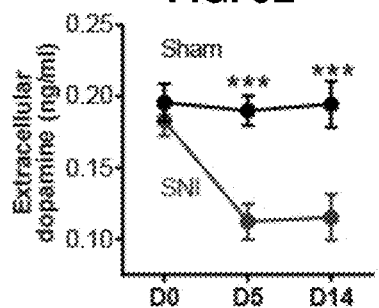
FIG. 6E is a graph showing results from a microdialysis examination comparing the dopamine level in NAc in SNI and sham animals at post-surgery Day 5 and Day 14 ($n=6$, $p<0.0001$, two way ANOVA).
Figure 6F:
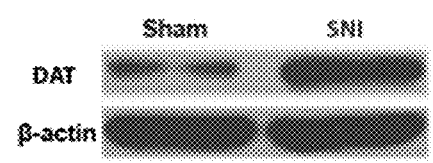
FIG. 6F is a representative photograph of a western blot bands to detect expression of dopamine transporter (DAT) in NAc of SNI and Sham animals.
Figure 6G:
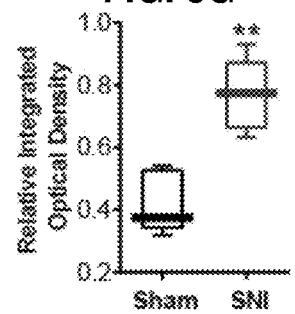
FIG. 6G is a graph showing the expression of DAT in NAc in SNI animals relative to sham animals ($n=5$, $p<0.01$, Mann-Whitney Utest).
Figure 6H:
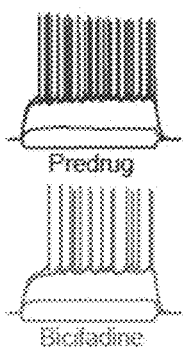
FIG. 6H is a set of graphs showing representative excitabilities of iSPNs before and after administering DAT antagonist bicifadine (20 µM) in SNI animals.
Figure 6I:
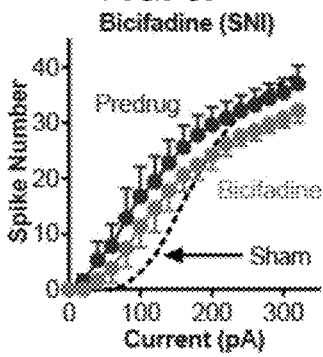
FIG. 6I is a graph showing the iSPN spike number as a function of current before and after administering bicifadine in SNI animals, relative to sham animals ($n=5$, $p<0.0001$, two-way ANOVA).
Figure 6J:
FIG. 6J is a set of graphs showing representative excitabilities of iSPNs before and after administering DAT antagonist GBR12909 (20 µM) in SNI animals.
Figure 6K:
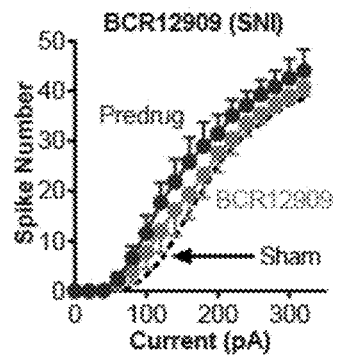
FIG. 6K is a graph showing the iSPN spike number as a function of current before and after administering GBR12909 in SNI animals, relative to sham animals ($n=5$, $p<0.01$, two-way ANOVA).

One potential explanation for this change is that extracellular dopamine was reduced in the SNI mice leading to diminished D2 receptor mediated inhibition of iSPNs excitability. To test this possibility, the extracellular dopamine concentration in the NAc was measured with a dialysis probe in awake SNI and sham rats. These experiments revealed that dopamine levels in SNI rats were significantly lower than in controls (FIG. 6E). There are two possible mechanisms for this change. One is decreased dopamine release by VTA neurons, possibly resulting from inhibition of their ongoing pacemaking. The other is increased dopamine uptake following up-regulation of dopamine transporter (DAT) expression. In keeping with the latter, the abundance of DAT protein in the NAc shell was increased in SNI mice (FIGS. 6F, 6G). Furthermore, bath application of the DAT antagonists bicifadine (20 µM) or GBR12909 (20 µM) decreased the excitability of iSPNs in slices from SNI mice (FIGS. 6H-6K). Taken together, these results show that SNI led to a drop in extracellular dopamine concentration in the NAc that was at least in part attributable to up-regulation of DAT expression.

Figure 7A:
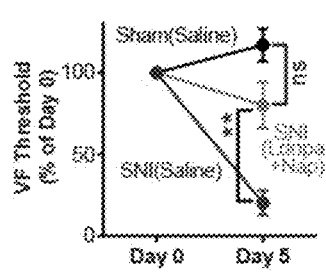
FIG. 7A is a graph showing the effect of oral naproxen and levodopa co-treatment on tactile responses in SNI mice after 5 days post-surgery ($n=6$ in each group, $p<0.0001$, two-way ANOVA followed by Tukey's multiple comparisons test).
Figure 7B:
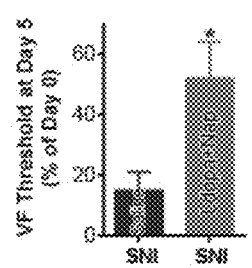
FIG. 7B is a bar graph showing the effect of levodopa and naproxen co-treatment on SNI-induced allodynia ($n=6$ in each group, $p<0.05$, student's t-test).
Figure 7C:
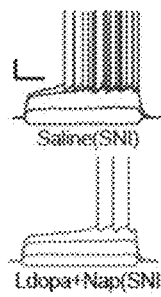
FIG. 7C is a set of representative traces showing excitabilities of iSPNs in response to saline or levodopa and naproxen co-treatment (calibration bars: 20 mV, 200 ms; current injections: −40, 20, 60 and 100 pA).
Figure 7D:
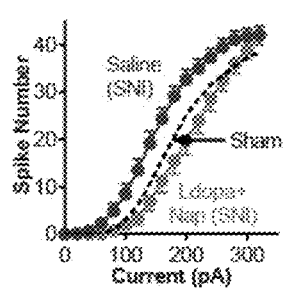
FIG. 7D is a graph showing the iSPN spike number as a function of current for SNI animals treated with either saline or co-treatment, relative to sham animals ($n=10$, $p<0.0001$, two-way ANOVA).
Figure 7E:
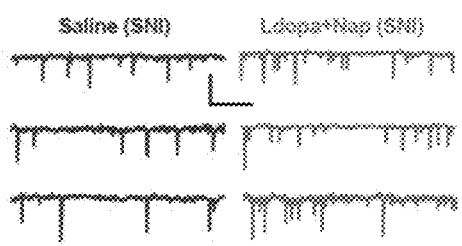
FIG. 7E is a set of representative mEPSC recordings from SNI animals receiving either saline or combination treatment (calibration bar: 20 pA, 400 ms).
Figure 7F:
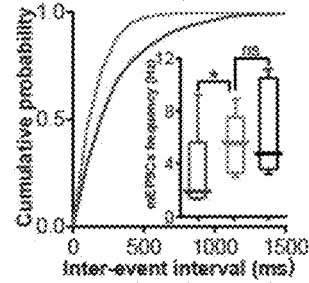
FIG. 7F is a set of graphs showing the mEPSC frequency of iSPNs of SNA animals receiving either saline or combination treatment ($n=7$-8, $p<0.05$, Kolmogorov-Smirnov test for Cumulative probability histograms and Mann-Whitney Utest for box plots).
Figure 7G:
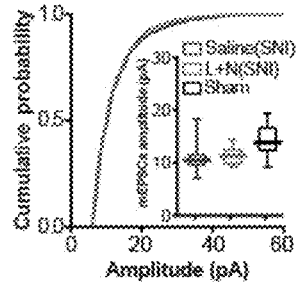
FIG. 7G is a set of graphs showing the mEPSC amplitude of iSPNs of SNA animals receiving either saline or combination treatment ($n=7$-8, $p>0.05$, Kolmogorov-Smirnov test for Cumulative probability histograms and Mann-Whitney U test for box plots).
Figure 7H:
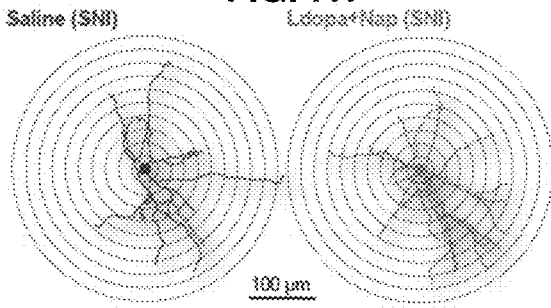
FIG. 7H is a set of representative three-dimensional Sholl reconstructions of iSPNs from SNI animals receiving either saline or combination treatment.
Figure 7I:
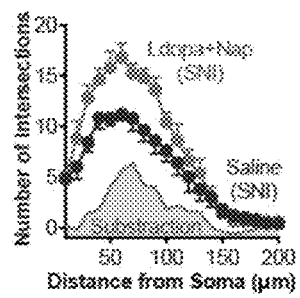
FIG. 7I is a graph showing the number of iSPN dendrite intersections as a function of the distance from the soma between SNI animals receiving either saline or combination treatment ($n=7$ in each group, $p<0.0001$, two-way ANOVA).
Figure 7J:
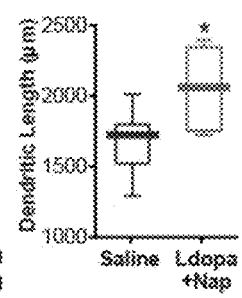
FIG. 7J is a graph comparing the iSPN dendritic length between SNI animals receiving either saline or combination treatment ($n=7$ in each group, $p<0.05$, Mann-Whitney Utest).
Figure 8D:
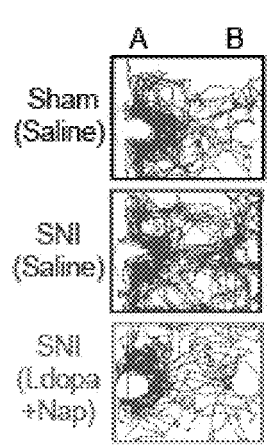
FIG. 8D is a set of representative tracks of the space explored by animals in each group during the sociability test.
Figure 8E:
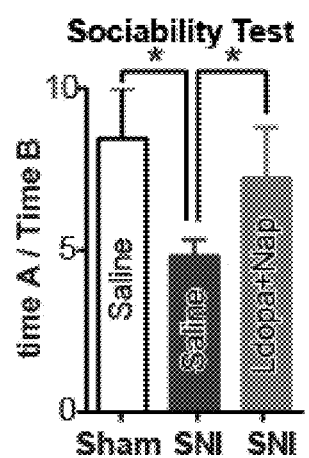
FIG. 8E is a bar graph showing the effect of levodopa and naproxen co-administration on sociability test performance, in comparison to saline controls ($n=8$-16 in each group, $p<0.05$, one-way ANOVA followed by Tukey's multiple comparisons test).

Example 5. Levodopa and Naproxen Treatment Reversed NAc Reorganization and Blunted Neuropathic Pain Behavior If the SNI-induced adaptations in the NAc were triggered by a decreased background dopamine concentration, then boosting dopamine level should prevent them. The standard approach to increase dopamine in the brain consists in the administering levodopa. To test this therapeutic strategy, mice were systemically administered levodopa (0.3 mg/kg) in combination with naproxen (30 mg/kg) and then subjected to the SNI procedure (within 2 hours). After 5 days of treatment, mice were assessed behaviorally and sacrificed. The combination of levodopa and naproxen prevented the physiological and structural adaptations in NAc iSPNs (FIGS. 7C-7J). Moreover, this combination prevented the development of SNI-induced tactile allodynia in mice (FIG. 7A, 7B) or rats (FIG. 8A). This combination also was effective in an inflammatory model of persistent pain induced by carrageenan injection in rats (FIG. 8B). Lastly, because tactile allodynia only constitutes one aspect of the neuropathic pain state (Navratilova et al, 2013, *Annals of the NYAS*, 1282, 1-11), the efficacy of the combination treatment on a social recognition task was examined. Levodopa with naproxen treatment effectively abolished the social recognition impairment observed in SNI rats (FIGS. 8C-8E).

Example 6. Treatment of Acute Pain

Figure 9:
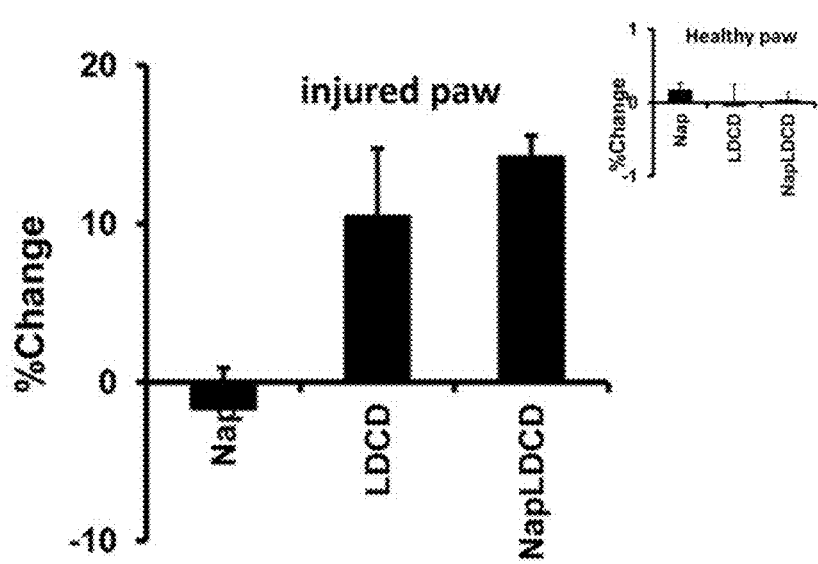
FIG. 9 is a bar graph showing the percentage of change of tactile allodynia after one hour of drug orally injected compared to baseline at day 5 after SNI surgery.

This example demonstrates the effect at day 5 after SNI surgery (acute treatment model). We used 24 Sprague Dawley male rats, weighting from 200-220 grams. They were divided into 3 groups: a) 8 animals receiving naproxen (30 mg/kg, 1.5 ml/kg); b) 8 animals receiving levodopa (1.5 mg/kg) and carbidopa (0.375 mg/kg), 1.5 mg/kg; and c) 8 animals received naproxen, levodopa, and carbidopa (same doses in groups a and b. The percentage of change of the tactile allodynia after 1 hour of drug orally injected compared to baseline at day 5 after SNI surgery is shown (FIG. 9).

Example 7. Treatment of Chronic Pain

Figure 10A:
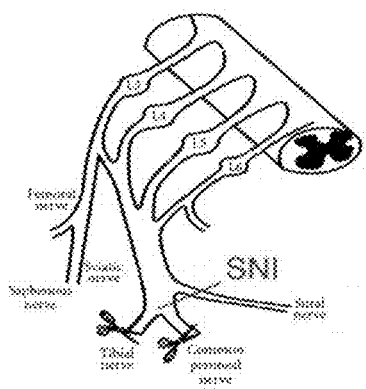
FIG. 10A is a schematic depicting the SNI procedure.
Figure 10B:
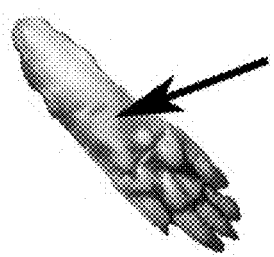
FIG. 10B is a photograph identifying the food pad carrageenan injection site.
Figure 10C:
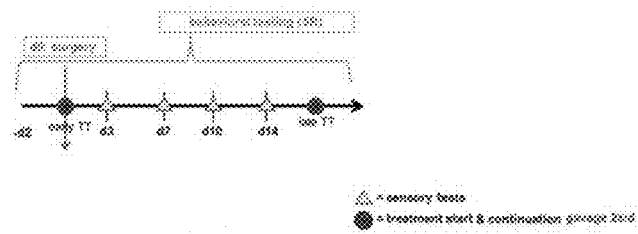
FIG. 10C is a timeline describing the SNI experiment.
Figure 10D:
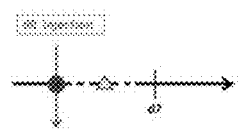
FIG. 10D is a timeline describing the carrageenan experiments.
Figure 11A:
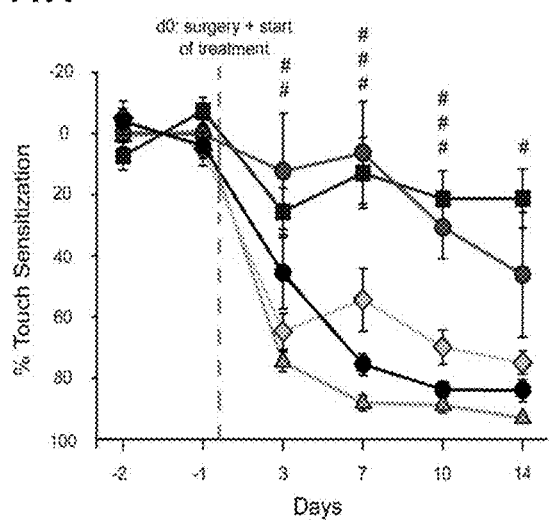
FIG. 11A is a graph showing the effects of levodopa, naproxen, and co-administration on VF thresholds over time after SNI injury as a percent change from baseline (mean±SEM, combination versus control post-hoc results are signified as #=$p<0.05$; ##=$p<0.005$; ###=$p<0.0005$, ANOVA.
Figure 11B:
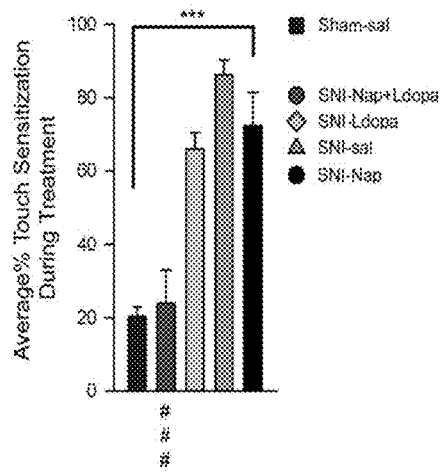
FIG. 11B is a bar graph showing the average percent change from baseline over the course of treatment (d0-d14, mean±SEM, combination versus control post-hoc results are signified as ###=$p<0.0005$, ANOVA $F(4,37)=27.462$, $p<0.0005$, ANOVA results are signified as *=$p<0.05$; =$p<0.005$; *=$p<0.0005$).
Figure 12A:
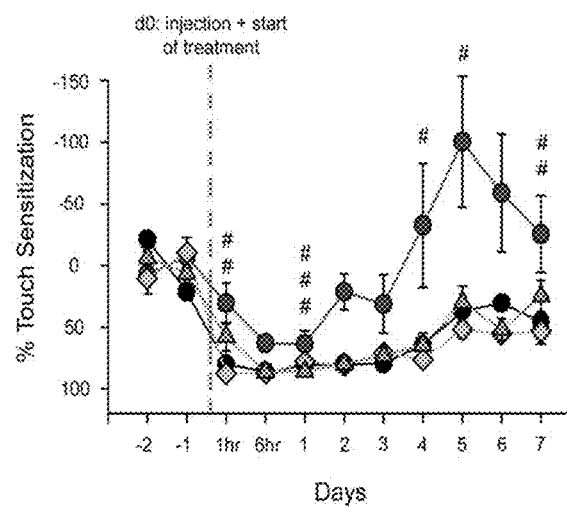
FIG. 12A is a graph showing the effects of levodopa, naproxen, and co-administration on VF thresholds over time after carrageenan injection as a percent change from baseline (mean±SEM, combination versus control post-hoc results are signified as #=$p<0.05$; ##=$p<0.005$; ###=$p<0.0005$, ANOVA.
Figure 12B:
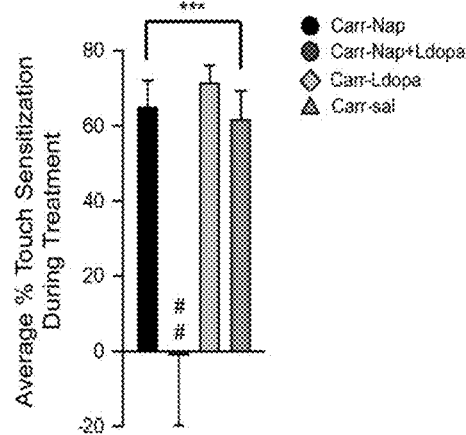
FIG. 12B is a bar graph showing the average percent change from baseline over the course of treatment (d0-d14)(mean±SEM, combination versus control post-hoc results are signified as ###=$p<0.0005$, ANOVA $F(3,28)=8.3997$, $p=0.00039$, ANOVA results are signified as =$p<0.05$;=$p<0.005$; *=$p<0.0005$).

This example demonstrates the effect of co-administering dopaminergic agents with naproxen on chronic pain. Animals were adult (~3 mo) male Sprague Dawley rats weighing ~300 g/ea (n=8-9 animals/group). We utilized 2 animal models of pain: 1) neuropathic pain (spared nerve injury, SNI) with appropriate sham controls (FIGS. 10A-10C), and 2) inflammatory pain (carrageenan injection, FIGS. 10B, 10D). Rats were administered a gavage of saline, naproxen (30 mg/kg), levodopa (1.5 mg/kg), or a combination of either levodopa with naproxen or levodopa with carbidopa (0.375 mg/kg) and naproxen. All drugs were dissolved in a saline (2 ml/kg). Treatment began ~2 hours before SNI injury or carrageenan injection (d0) and was continued twice a day for the duration of the study. Von-Frey thresholds were tested throughout the length of treatment, as well other behaviors such as open field (not shown) and social recognition. Results demonstrate that co-administering levodopa with naproxen blocks tactile allodynia in SNI (FIGS. 11A-11B) and in carrageenan model (FIGS. 12A-12B). In SNI animals, the combination of levodopa and naproxen blocked characteristic tactile allodynia for a little under 2 weeks before its effects gradually went away. In carrageenan animals, it diminished tactile allodynia in its early and late phases and led to an early recovery to baseline thresholds. These effects were significant in both models.

The implications of our results are important, as they: 1) represent potential treatment options for both early stage inflammatory and nerve injury pain, as well as for post-surgical pain relief and prevention, and 2) highlight the importance of early treatment on some of the social/cognitive changes that take place in the presence of prolonged pain.

Example 8. Social Discrimination is Impaired in SNI Animals that Did not Receive Early Treatment of Levodopa with Naproxen Social recognition is the ability of an animal to distinguish conspecifics (e.g. a new animal from an old animal). It has 3 stages: 1) habituation, 2) social ability, and 3) social discrimination. Social ability refers to the animal's preference to of another animal over an inanimate object, while social discrimination refers to an animal's preference of an unknown animal over a known animal. Poor performance in one or both of the latter 2 stages indicates social impairment.

Figure 13A:
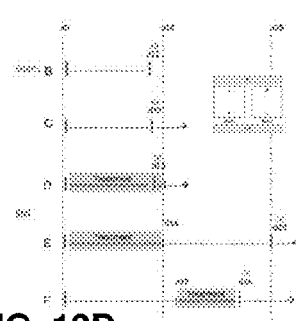
FIG. 13A is a timeline of the social discrimination SNI experiments of FIGS. 13B-13F, and the inset figure shows the experimental setup (mean±SEM, $p<0.05$).
Figure 13B:
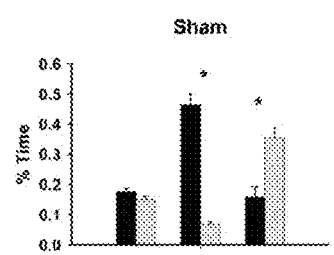
FIG. 13B is a bar graph showing that social ability (Rec) and social discrimination (Disc) are intact in Sham animals (mean±SEM, $p<0.05$).
Figure 13C:
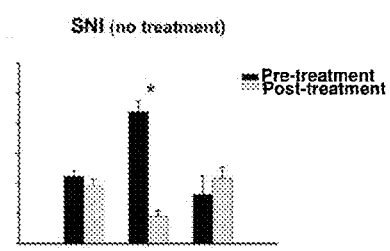
FIG. 13C is a bar graph showing that social discrimination (Disc) is impaired in SNI animals receiving no treatment (mean±SEM, $p<0.05$).
Figure 13D:
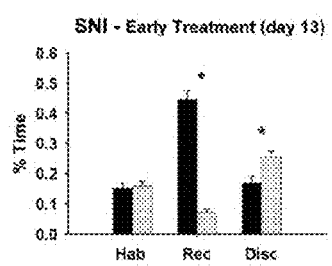
FIG. 13D is a bar graph showing that social ability (Rec) and social discrimination (Disc) are intact in SNI animals receiving early treatment (mean±SEM, $p<0.05$).
Figure 13E:
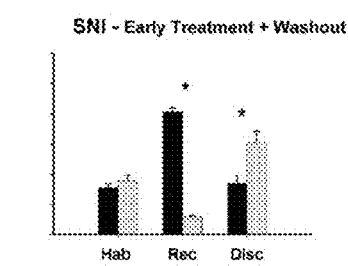
FIG. 13E is a bar graph showing that social ability (Rec) and social discrimination (Disc) are intact in SNI animals with 14 days of treatment starting the day of the surgery followed by 15 days of washout. The test was performed 19 days after surgery (mean±SEM, $p<0.05$).
Figure 13F:
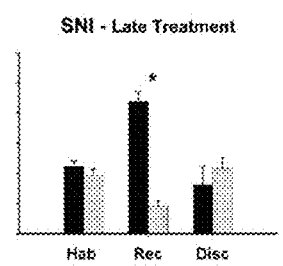
FIG. 13F is a bar graph showing that social discrimination (Disc) is impaired in SNI animals with 8 days of treatment starting at day 17 after SNI surgery (late treatment). The test was performed 26 days after surgery (mean±SEM, $p<0.05$).

Animals under treatment received a combination of naproxen (30 mg/kg), levodopa (1.5 mg/kg), and carbidopa (0.375 mg/kg). Each stage of the experiments lasted 10 minutes with a 5 minute inter-trial intervals, as shown in the experimental setup (FIG. 13A). In Sham animals, social discrimination (Disc) was intact (FIG. 13B). In untreated SNI animals, Disc was impaired (FIG. 13C). In SNI animals treated 13 days after surgery (with 13 days of treatment), Disc was intact (FIG. 13D). In SNI animals receiving treatment for 14 days, followed by 15 days of washout, Disc was intact (FIG. 13E). In SNI animals receiving 8 days of treatment starting at day 17 (late treatment), Disc was impaired (FIG. 13F).

Social discrimination was intact only in Sham animals or those SNI animals that received early treatment. In contrast to the sensory test results (which showed no treatment effect on allodynia past 14 days), social recognition results indicated a higher-level (central) effect of early treatment that lasts throughout treatment and continues even after 15 days of washout. These studies highlight the importance of early treatment on some of the social/cognitive changes that take place in the presence of prolonged pain, and the implications of these results represent potential treatment options for both early stage inflammatory and nerve injury pain, as well as for post-surgical pain relieve and prevention.

Example 9. Pramipexole Treatment

Figure 14:
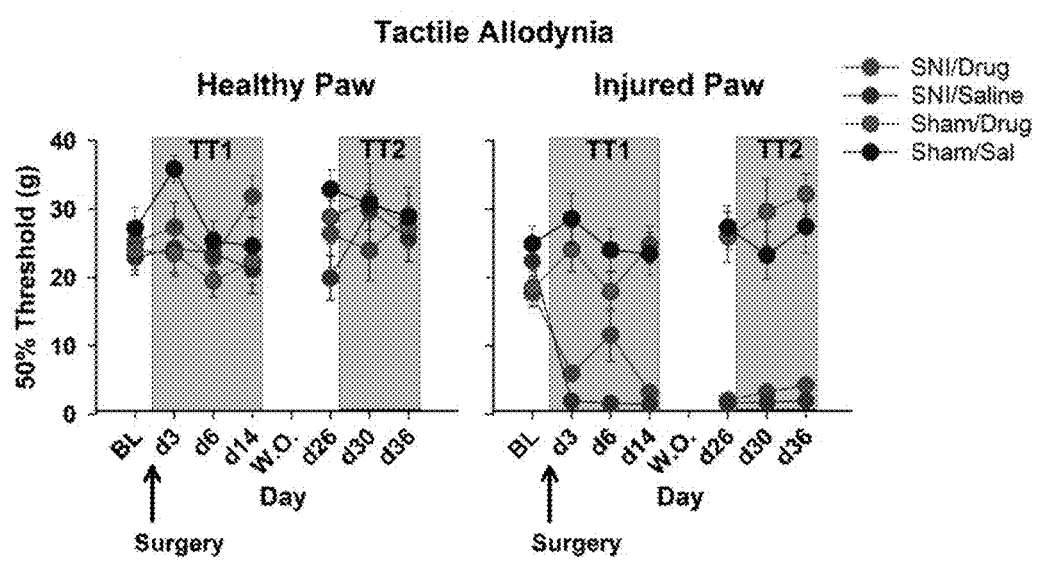
FIG. 14 is a set of graphs showing the kinetic profiles of tactile allodynia during acute (TT1) and chronic (TT2) pain, as a result of pramipexole treatment in an SNI model.
Figure 15:
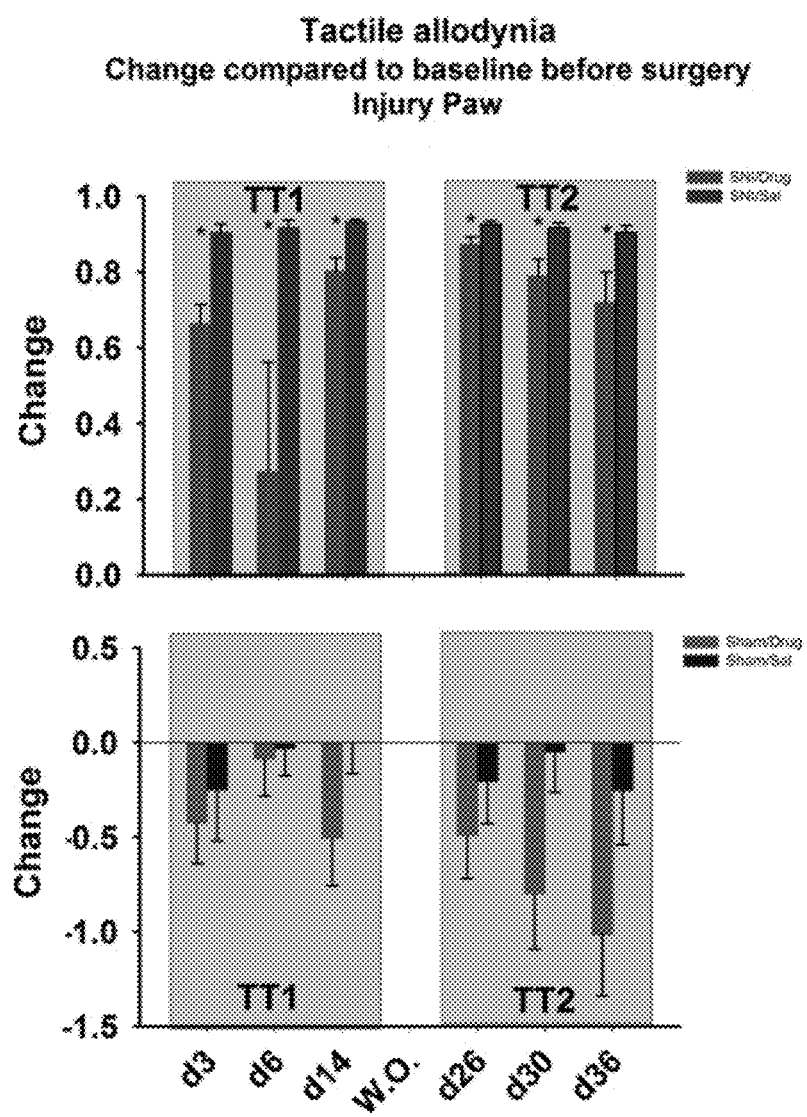
FIG. 15 is a set of bar graphs showing tactile allodynia relative to baseline before surgery during acute (TT1) and chronic (TT2) pain, as a result of pramipexole treatment in an SNI model.
Figure 16:
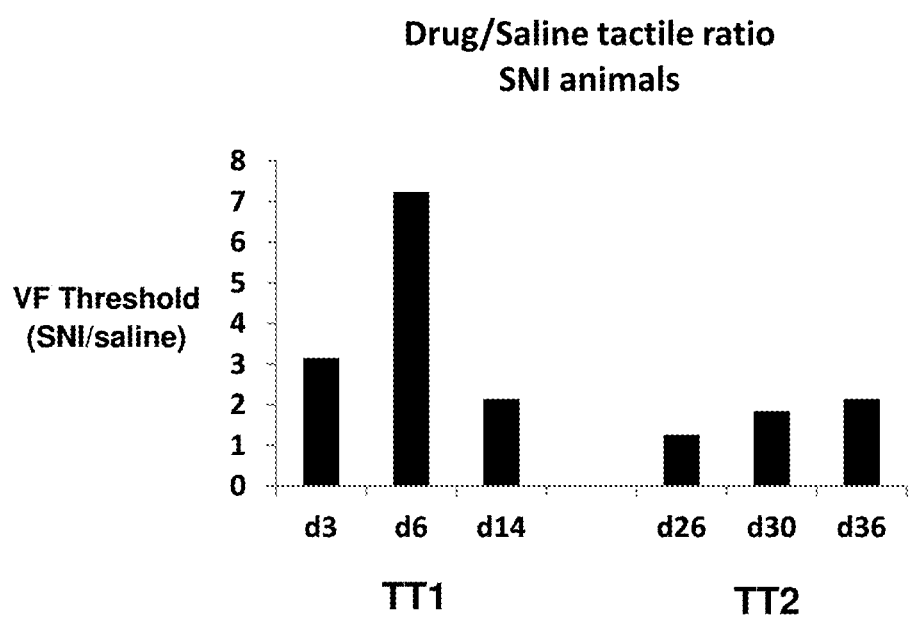
FIG. 16 is a bar graph showing VF thresholds between SNI drug and saline treatment during Treatment 1 (TT1) and Treatment 2 (TT2).
Figure 17:
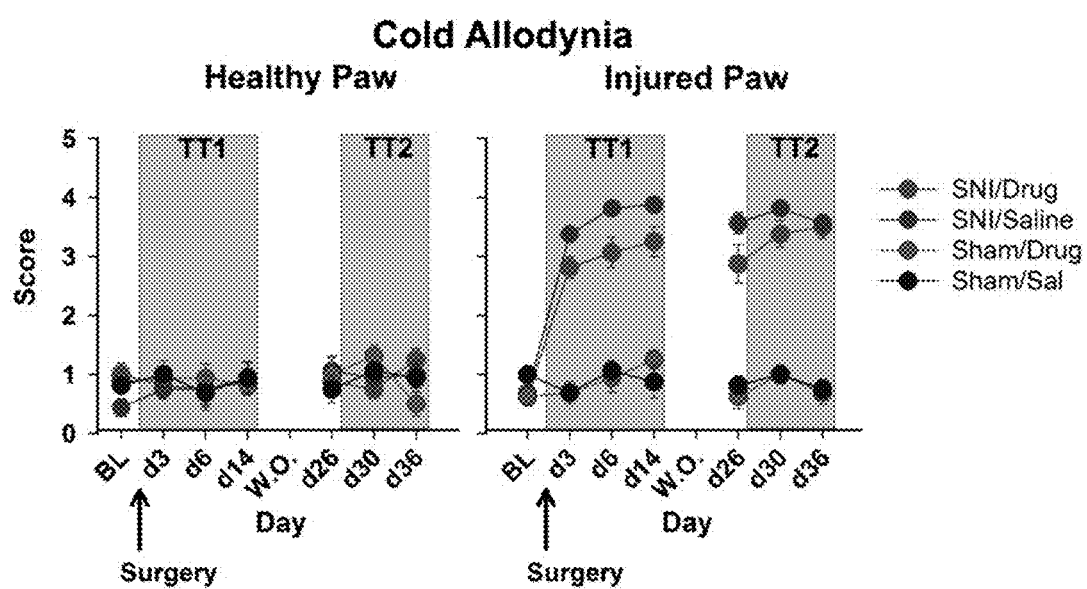
FIG. 17 is a set of graphs showing the kinetic profiles of cold allodynia during acute (TT1) and chronic (TT2) pain, as a result of pramipexole treatment in an SNI model.

This example demonstrates the use of pramipexole as a D2 agonist, in conjunction with naproxen, an analgesic, as part of the current invention. Animals were adult (~3 mo) male Sprague Dawley rats weighing ~300 g/ea (n=8 animals/group, 4 groups total). We utilized the SNI neuropathic pain model with appropriate sham. Von-Frey thresholds were tested throughout the length of experiment. In Treatment 1 (TT1), treatment began ~2 hours before SNI injury (d0) and was continued twice a day for until day 14 after surgery. Rats were administered s.c. pramipexole (0.2 mg/kg; 1 ml/kg) or saline (1 ml/kg). In Treatment 2 (TT2), rats were administered either Pramipexole (0.2 mg/kg; 1 ml/kg, s.c.) with naproxen (30 mg/kg, 2 ml/kg p.o.) or saline (1 ml/kg, s.c.) with naproxen (30 mg/kg, 2 ml/kg, p.o.) during 10 days (from day 26 to day 36 after surgery) after a period of 12 days of washout after the first treatment. The kinetic profile of Von Frey thresholds as a result of treatment groups are shown (FIG. 14). These results are presented in bar graph form, relative to baseline values before surgery (FIG. 15). Drug/Saline tactile ratios in SNI animals (FIG. 16) show that only Von Frey thresholds between SNI Drug and saline treatment are significantly different during TT1 and TT2. Drug treatment yielded a significantly better score during TT1 relative to saline controls as measured by cold allodynia (FIG. 17).

Example 10. Mice Experiments

Figure 18A:
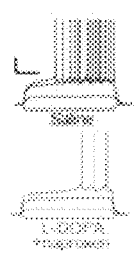
FIG. 18A is set of graphs showing representative excitabilities of iSPNs in mice receiving saline or levodopa+naproxen co-treatment.
Figure 18B:
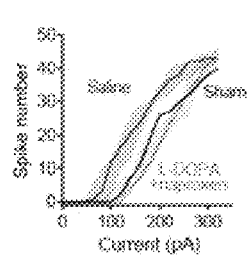
FIG. 18B is a graph showing the iSPN spike number as a function of current in mice receiving saline or levodopa+naproxen co-treatment, relative to Sham controls (n=8-10).
Figure 18C:
FIG. 18C is a set of representative mEPSC recordings from SNI mice receiving either saline or levodopa+naproxen co-treatment.
Figure 18D:
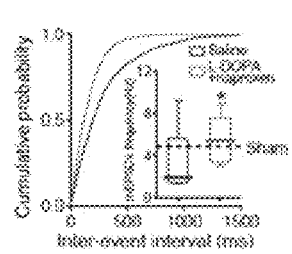
FIG. 18D is a set of graphs showing the mEPSC frequency of iSPNs of mice receiving either saline or levodopa+naproxen co-treatment, relative to sham controls (n=8-10).
Figure 18E:
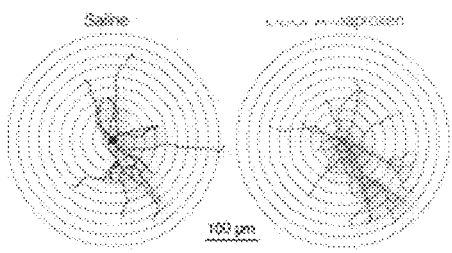
FIG. 18E is a set of representative three-dimensional Sholl reconstructions of iSPNs from SNI mice receiving either saline or levodopa+naproxen co-treatment.
Figure 18F:
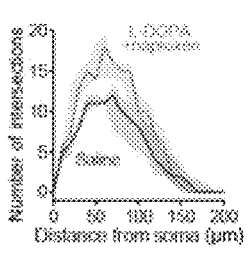
FIG. 18F is a graph showing the number of iSPN dendrite intersections as a function of the distance from the soma between SNI mice receiving either saline or levodopa+naproxen co-treatment (n=7).
Figure 18G:
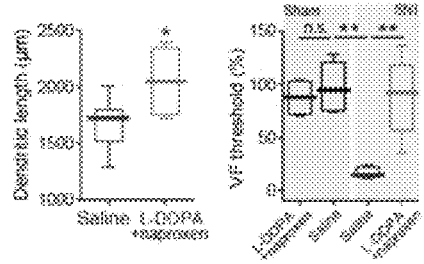
FIG. 18G is a graph comparing the iSPN dendritic length between SNI mice receiving either saline or levodopa+naproxen co-treatment (n=5-8).
Figure 18H:
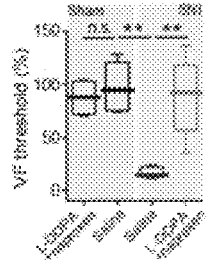
FIG. 18H is a graph showing the effect of levodopa and naproxen co-treatment on VF threshold in SNI mice relative to sham mice (n=5-8).

This example demonstrates that the effects observed in rats in response to the current compositions can be applicable to other species. Specifically, levodopa and naproxen combined treatment prevented SNI-induced reorganization of iSPNs and blunted tactile allodynia in mice (FIG. 18). In SNI animals, combined treatment restored the physiological adaptions (FIGS. 18A-18D) and dendritic complexity (FIGS. 18E, 18F) of iSPNs to sham level. Combined treatment blocked tactile allodynia in SNI and reverses SNI-induced social ability impairment (FIGS. 18G, 18H).

Example 11. Synergy Between Dopaminergic Agent and Analgesic Agents

This example demonstrates that combination treatment of both dopaminergic and analgesic agents are required for the benefit observed in both the SNI and the carrageenan models (FIG. 19). Combined treatment (but not either alone) blocked the development of tactile allodynia in SNI rats (FIG. 19A). Combined treatment (but not individual) rapidly reversed inflammatory tactile allodynia induced by carrageenan injection into the rat hind paw (FIG. 19B). The sociability test setup and representative results are shown (FIG. 19C). Combined treatment restored the interaction ability SNI rats compared with saline treated animals (FIG.

19D). Pramipexole treatment relieved the pain from SNI animals compared to saline treated ones (FIG. 19E).

Example 12. Treating Acute Pain in a Subject

A subject (e.g., a human patient) suffering from acute pain (e.g., pain resulting from trauma) can be treated by administering a D1 agonist (e.g., levodopa) and an analgesic agent (e.g., naproxen) at a molar ratio of between about 1:100 and 1:4 (e.g., 1:20), respectively. The D1 agonist and the analgesic agent can be administered in admixture or in separate dosage forms. For example, a tablet containing 10 mg levodopa and 200 mg naproxen can be orally administered to the subject. The subject can take the tablet once or more per day, every day, over the course of a month or longer, or until the pain subsides.

Example 13. Preventing the Transition from Acute to Chronic Pain in a Subject

A subject (e.g., a human patient) suffering from acute pain with associated risk of developing chronic pain (e.g., pain associated with surgical procedures known to involve risk for chronic pain development) can be treated by administering a D2 agonist, a D1 agonist, and an analgesic agent (e.g., carbidopa, levodopa, and naproxen). The D2 agonist, D1 agonist, and analgesic agent can be administered at a molar ratio of about 1:4:80, respectively, and can be administered soon after the onset of acute pain. For example, a tablet containing 12.5 mg carbidopa and 50 mg levodopa can be administered once per day in parallel with a daily dose of a 1000 mg tablet of naproxen. Alternatively, a tablet containing all three drugs (i.e., carbidopa, levodopa, and naproxen) at a 1:4:80 molar ratio can be administered once or more per day, throughout the duration of acute pain.

Example 14. Treating Chronic Pain in a Subject

A subject (e.g., a human patient) suffering from chronic pain (e.g., chronic back pain) can be treated by administering a D2 agonist (e.g., pramipexole) and an analgesic agent (e.g., naproxen) at a molar ratio of between about 1:600 and 1:30 (e.g., 1:150), respectively. The D2 agonist and the analgesic agent can be administered in admixture or as separate dosage forms. For example, a tablet containing 1.0 mg pramipexole and 150 mg naproxen can be orally administered to the subject. The subject can take the tablet once or more per day, every day, over the course of a month or longer, or until the pain subsides.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the claims.

Other embodiments are within the claims.

The invention claimed is:

1. A method of reducing pain in a subject in need thereof, said method comprising administering to the subject a dopaminergic agent and a non-steroidal anti-inflammatory drug (NSAID) every day at a ratio of 1:20 to 1:4 for a total treatment period of up to, but no longer than, one month.

2. The method of claim 1, wherein
the dopaminergic agent comprises a D1 agonist, a D2 agonist, or a combination thereof.

3. The method of claim 1, wherein the NSAID is selected from the group consisting of naproxen, aceclofenac, acemetacin, acetaminophen, aloxiprin, aspirin, benorilate, bromfenac, celecoxib, deracoxib, diclofenac, diflunisal, ethenzamide, etodolac, etofenamate, etoricoxib, fenbufen, fenoprofen, flufenamic acid, flurbiprofen, lonazolac, lornoxicam, ibuprofen, indomethacin, isoxicam, kebuzone, ketoprofen, ketorolac, licofelone, loxoprofen, lumiracoxib, meclofenamic acid, mefenamic acid, meloxicam, metamizol, mofebutazone, nabumetone, niflumic acid, nimesulide, oxaprozin, oxyphenbutazone, parecoxib, phenidone, phenylbutazone, piroxicam, propacetamol, propyphenazone, rofecoxib, salicylamide, sulfinpyrazone, sulindac, suprofen, tiaprofenic acid, tenoxicam, tolmetin, and valdecoxib.

4. The method of claim 1, wherein the pain is acute pain, wherein the administering occurs no earlier than two months prior to the onset of the acute pain or no later than 3 months after the onset of the acute pain.

5. The method of claim 1, wherein the ratio of the dopaminergic agent to the NSAID is 1:10, 1:8, 1:6, 1:5, or 1:4.

6. The method of claim 1, wherein the dopaminergic agent comprises a D1 agonist.

7. The method of claim 6, wherein the D1 agonist is levodopa.

8. The method of claim 1, wherein the dopaminergic agent comprises levodopa and carbidopa.

9. The method of claim 8, wherein the ratio of levodopa to carbidopa to the NSAID is 1:4:80, respectively.

10. The method of claim 1, wherein the pain is persistent pain and wherein:
the persistent pain is peripheral neuropathic pain, postherpetic neuralgia, diabetic neuropathic pain, neuropathic cancer pain, failed back-surgery syndrome, trigeminal neuralgia, phantom limb pain, central neuropathic pain, multiple sclerosis related pain, Parkinson disease-related pain, post-stroke pain, post-traumatic spinal cord injury pain, pain from dementia, musculoskeletal pain, osteoarthritic pain, fibromyalgia syndrome, inflammatory pain, rheumatoid arthritis, endometriosis, migraine, cluster headache, tension headache syndrome, facial pain, headache caused by other diseases, visceral pain, interstitial cystitis, irritable bowel syndrome, chronic pelvic pain syndrome, lower back pain, neck and shoulder pain, burning mouth syndrome, or complex regional pain syndrome.

11. The method of claim 2, wherein the D2 agonist is pramipexole or carbidopa.

12. The method of claim 1, wherein the method further comprises administering an additional therapeutic agent, an antidepressant, an anti-inflammatory agent, a chemotherapeutic agent, a steroid, or a muscle relaxant.

13. The method of claim 12, wherein the additional therapeutic agent is administered:

i) at a different time from the dopaminergic agent or the NSAID;
ii) at the same time as the dopaminergic agent or the NSAID;
iii) through a different route from the dopaminergic agent or the NSAID; or
iv) through the same route as the dopaminergic agent or the NSAID.

14. The method of claim 1, wherein the dopaminergic agent or the NSAID is administered in an amount of 5 mg to 2,000 mg per dose.

15. The method of claim 14, wherein the dopaminergic agent or the NSAID is administered in an amount of 10 mg to 1,000 mg per dose.

16. The method of claim 15, wherein the dopaminergic agent or the NSAID is administered in an amount of 20 mg to 500 mg per dose.

17. The method of claim 1, wherein the subject is a human.

18. The method of claim 1, wherein the dopaminergic agent is levodopa, carbidopa, or a combination thereof; and wherein the NSAID is naproxen.

19. The method of claim 18, wherein the naproxen is in an amount of 10 mg to 1,000 mg per dose.

20. The method of claim 19, wherein the naproxen is in an amount of 20 mg to 500 mg per dose.

21. The method of claim 20, wherein the naproxen is in an amount of 50 mg, 100 mg, 250 mg, 500 mg, 1,000 mg, or 2,000 mg per dose.

22. The method of claim 18, wherein the dopaminergic agent comprises:
i) levodopa in an amount of 50 mg per dose and carbidopa in an amount of 12.5 mg per dose;
ii) levodopa in an amount of 100 mg per dose and carbidopa in an amount of 25 mg per dose; or
iii) levodopa in an amount of 200 mg per dose and carbidopa in an amount of 50 mg per dose.

23. The method of claim 18, wherein:
the dopaminergic agent comprises levodopa in an amount of 50 mg per dose and carbidopa in an amount of 12.5 mg per dose, and the naproxen is in an amount of 250 mg per dose.

24. The method of claim 1, wherein the dopaminergic agent and the NSAID are administered three times per day.

25. The method of claim 19, wherein the dopaminergic agent and the NSAID are coadministered in a pharmaceutical composition comprising a pharmaceutically acceptable carrier or excipient.

26. The method of claim 1, wherein the administering occurs prior to the onset of acute pain.

27. The method of claim 1, wherein the administering occurs after the onset of acute pain.

28. The method of claim 1, wherein the dopaminergic agent and the NSAID are not administered to the subject other than during the one month.

29. The method of claim 1, wherein the pain is acute pain.

30. The method of claim 1, wherein the pain is persistent pain.

* * * * *